(12) United States Patent
Jenkins et al.

(10) Patent No.: US 10,137,285 B2
(45) Date of Patent: Nov. 27, 2018

(54) BALLOON DILATION SYSTEM WITH MALLEABLE INTERNAL GUIDE

(71) Applicant: Acclarent, Inc., Menlo Park, CA (US)

(72) Inventors: Thomas R. Jenkins, Alameda, CA (US); Randy J. Kesten, Mountain View, CA (US); Siddhi K. Desai, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 410 days.

(21) Appl. No.: 14/824,435

(22) Filed: Aug. 12, 2015

(65) Prior Publication Data

US 2016/0310714 A1 Oct. 27, 2016

Related U.S. Application Data

(60) Provisional application No. 62/150,945, filed on Apr. 22, 2015.

(51) Int. Cl.
*A61M 29/02* (2006.01)
*A61B 1/233* (2006.01)
(Continued)

(52) U.S. Cl.
CPC ......... *A61M 29/02* (2013.01); *A61B 1/00066* (2013.01); *A61B 1/00183* (2013.01); *A61B 1/07* (2013.01); *A61B 1/233* (2013.01); *A61M 25/0041* (2013.01); *A61M 25/09025* (2013.01); *A61B 1/32* (2013.01); *A61B 17/24* (2013.01); *A61B 2017/00946* (2013.01); *A61M 2025/0915* (2013.01); *A61M 2025/09116* (2013.01);
(Continued)

(58) Field of Classification Search
CPC . A61M 29/02; A61B 1/00183; A61B 1/00066
See application file for complete search history.

(56) References Cited

U.S. PATENT DOCUMENTS 4,899,741 A * 2/1990 Bentley ................. A61B 18/28
374/141
5,040,543 A * 8/1991 Badera ............ A61M 25/09025
600/434
(Continued)

FOREIGN PATENT DOCUMENTS

EP 0715865 6/1996
EP 1195174 4/2002
(Continued)

OTHER PUBLICATIONS

U.S. Appl. No. 62/150,945, filed Apr. 22, 2015.
International Search Report and Written Opinion dated Jul. 5, 2016 re Application No. PCT/US2016/026909.

*Primary Examiner* — Richard Louis
(74) *Attorney, Agent, or Firm* — Frost Brown Todd LLC

(57) ABSTRACT

An apparatus includes a handle assembly, a guide assembly, and a dilation catheter. The guide assembly extends distally from the handle assembly. The guide assembly includes a malleable guide member and a flexible guide member. The distal end of the flexible guide member is distal to the distal end of the malleable guide member. The flexible guide member is positioned about the malleable guide member and is slidable along the malleable guide member. The dilation catheter is slidably disposed about the flexible guide member.

20 Claims, 25 Drawing Sheets

(51) Int. Cl.
*A61M 25/00* (2006.01)
*A61M 25/09* (2006.01)
*A61B 1/07* (2006.01)
*A61B 1/00* (2006.01)
*A61B 17/24* (2006.01)
*A61B 1/32* (2006.01)
*A61B 17/00* (2006.01)

(52) U.S. Cl.
CPC ............ *A61M 2025/09175* (2013.01); *A61M 2029/025* (2013.01); *A61M 2205/582* (2013.01); *A61M 2210/0681* (2013.01)

(56) References Cited

U.S. PATENT DOCUMENTS

| | | | |
|---|---|---|---|
| 5,762,615 A * | 6/1998 | Weier | A61M 25/09 600/585 |
| 5,820,592 A | 10/1998 | Hammerslag | |
| 5,826,576 A | 10/1998 | West | |
| 5,882,333 A | 3/1999 | Schaer et al. | |
| 5,987,344 A | 11/1999 | West | |
| 6,511,471 B2 | 1/2003 | Rosenman et al. | |
| 6,849,062 B2 | 2/2005 | Kantor | |
| 7,044,921 B2 * | 5/2006 | Asmus | A61M 25/09 128/898 |
| 7,048,711 B2 | 5/2006 | Rosenman et al. | |
| 7,056,314 B1 | 6/2006 | Florio et al. | |
| 7,117,039 B2 | 10/2006 | Manning et al. | |
| 7,630,676 B2 | 12/2009 | Pirwitz | |
| 9,155,492 B2 | 10/2015 | Jenkins et al. | |
| 2002/0072689 A1 * | 6/2002 | Klint | A61M 25/09025 600/585 |
| 2002/0082523 A1 * | 6/2002 | Kinsella | A61M 25/09 600/585 |
| 2005/0070986 A1 * | 3/2005 | Tockman | A61N 1/056 607/122 |
| 2008/0183128 A1 | 7/2008 | Morriss et al. | |
| 2008/0228085 A1 * | 9/2008 | Jenkins | A61B 1/00071 600/478 |
| 2010/0030031 A1 | 2/2010 | Goldfarb et al. | |
| 2010/0168511 A1 | 7/2010 | Muni et al. | |
| 2011/0004057 A1 | 1/2011 | Goldfarb et al. | |
| 2013/0274715 A1 | 10/2013 | Chan et al. | |

FOREIGN PATENT DOCUMENTS

| | | |
|---|---|---|
| EP | 2491974 | 8/2012 |
| JP | 10-34376 A | 2/1989 |
| JP | 6-017751 U | 3/1994 |
| JP | 2000-126303 A | 5/2000 |
| JP | 2004-049583 A | 2/2004 |
| JP | 2005-323702 A | 11/2005 |
| WO | WO 2000/067834 | 11/2000 |
| WO | WO 2001/068178 | 9/2001 |

* cited by examiner

//B BALLOON DILATION SYSTEM WITH MALLEABLE INTERNAL GUIDE

PRIORITY

This application claims priority to U.S. Provisional Patent App. No. 62/150,945, entitled "Balloon Dilation System with Malleable Internal Guide," filed Apr. 22, 2015, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492 issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
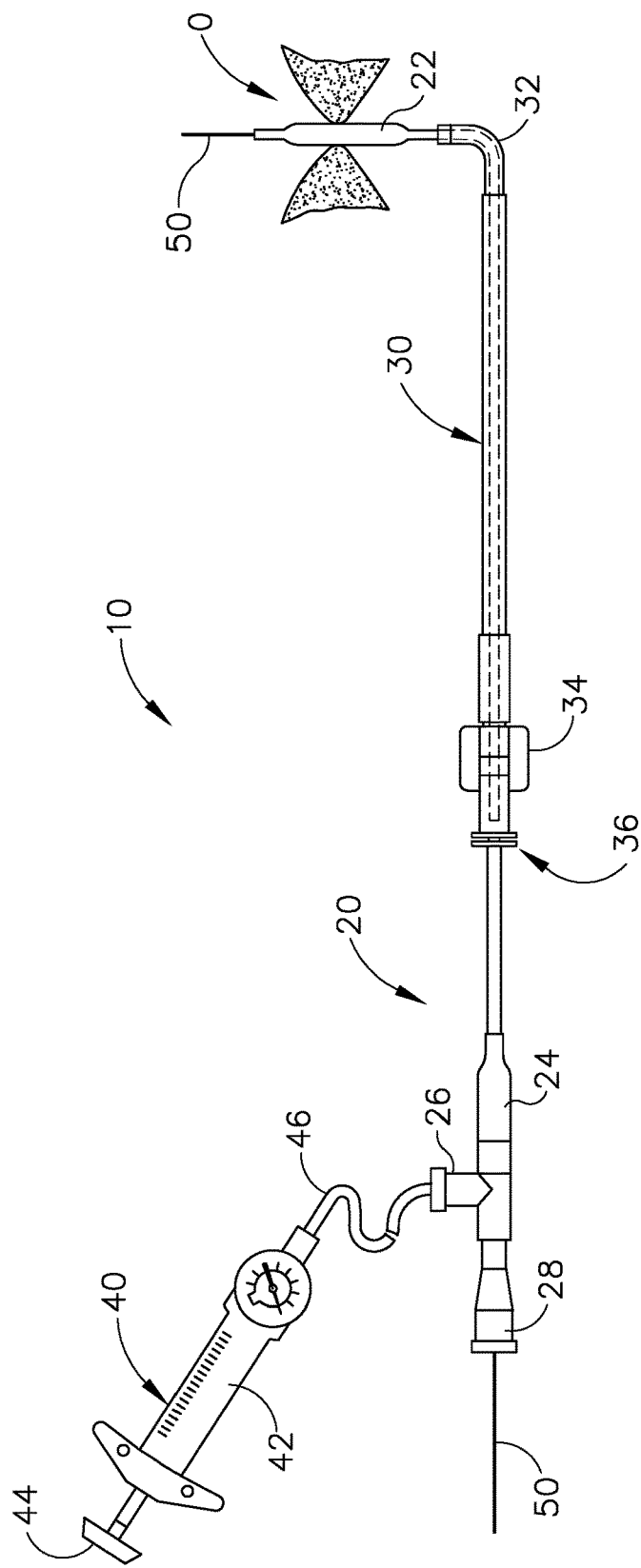
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26).

Figure 2:
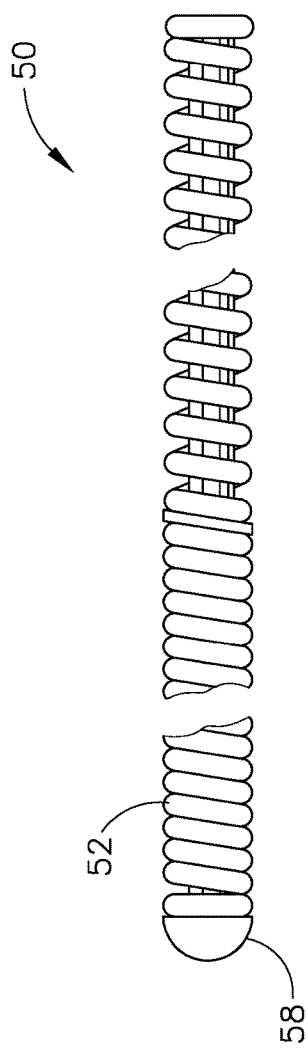
FIG. 2 depicts a side elevational view of an exemplary illuminating guidewire suitable for use with the dilation catheter system of FIG. 1.
Figure 3:
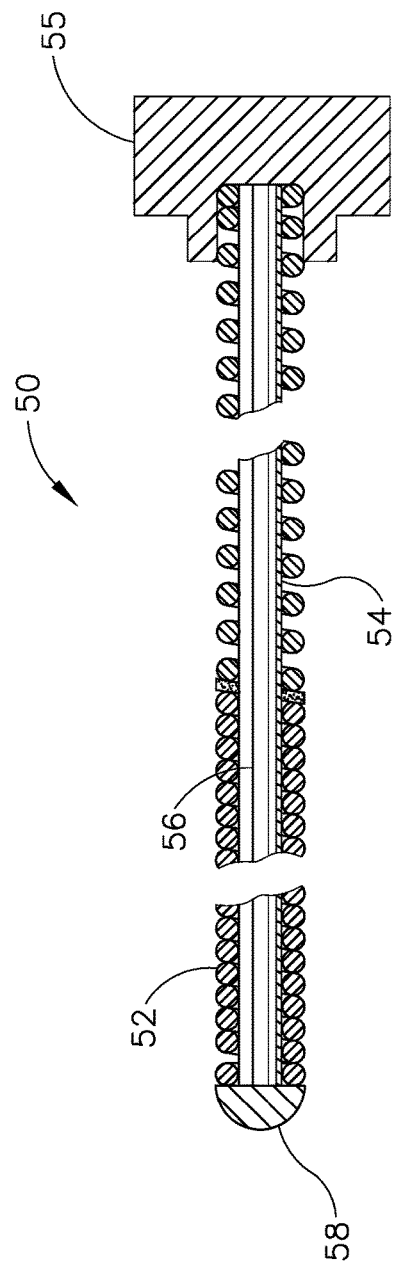
FIG. 3 depicts a side cross-sectional view of the illuminating guidewire of FIG. 2.

As best seen in FIGS. 2-3, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492 issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination fiber (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

In some instances, it may be desirable to irrigate the sinus and paranasal cavity after dilation catheter (20) has been used to dilate an ostium (O). Such irrigation may be performed to flush out blood, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

II. Overview of Exemplary Endoscope

Figure 4:
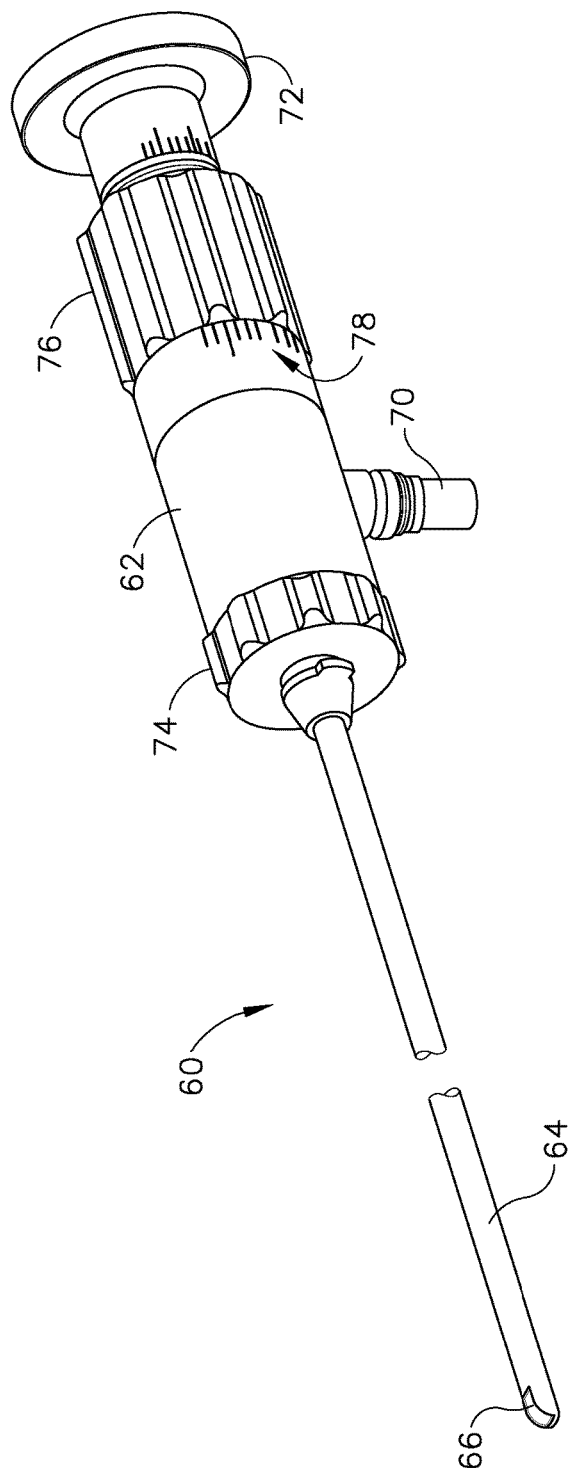
FIG. 4 depicts a perspective view of an exemplary endoscope suitable for use with the dilation catheter system of FIG. 1.
Figure 5:
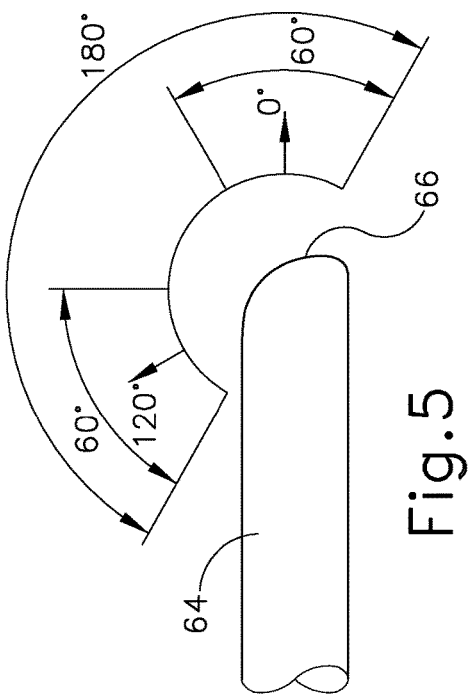
FIG. 5 depicts a side elevational view of the distal end of the endoscope of FIG. 4, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Alternative Dilation System with Malleable Internal Guide

As noted above, guide catheter (30) of dilation catheter system (10) has a bent distal end (32). The bend angle of bent distal end (32) may be selected to facilitate access to a drainage passageway associated with a particular paranasal sinus. For instance, the bend angle may be selected to facilitate access to the frontal recess. Alternatively, the bend angle may be selected to facilitate access to the ostium (O) of the maxillary sinus. Alternatively, the bend angle may be selected to facilitate access to the ostium (O) of the sphenoid sinus. Alternatively, the bend angle may be selected to facilitate access to a drainage passageway associated with the ethmoid sinus. The operator may thus be presented with a kit having several guide catheters (30) with different bend angles at the distal end (32), such that the operator may select a particular guide catheter (30) from the kit based on the drainage passageway that the operator wishes to dilate.

Alternatively, it may be desirable to provide a single instrument that is capable of achieving various different bend angles, such that the same single instrument may be used to access drainage passageways associated with various paranasal sinuses. Having such an instrument would avoid the need for accommodating a kit of several instruments and may thus avoid the need to select a particular instrument from the kit. An example of such a multi-sinus instrument is described in greater detail below. It should be understood that the instrument described below may nevertheless have at least some of the features and/or functionalities that are provided through dilation catheter system (10) describe above. Other suitable features and functionalities will be apparent to those of ordinary skill in the art in view of the teachings herein.

Figure 6:
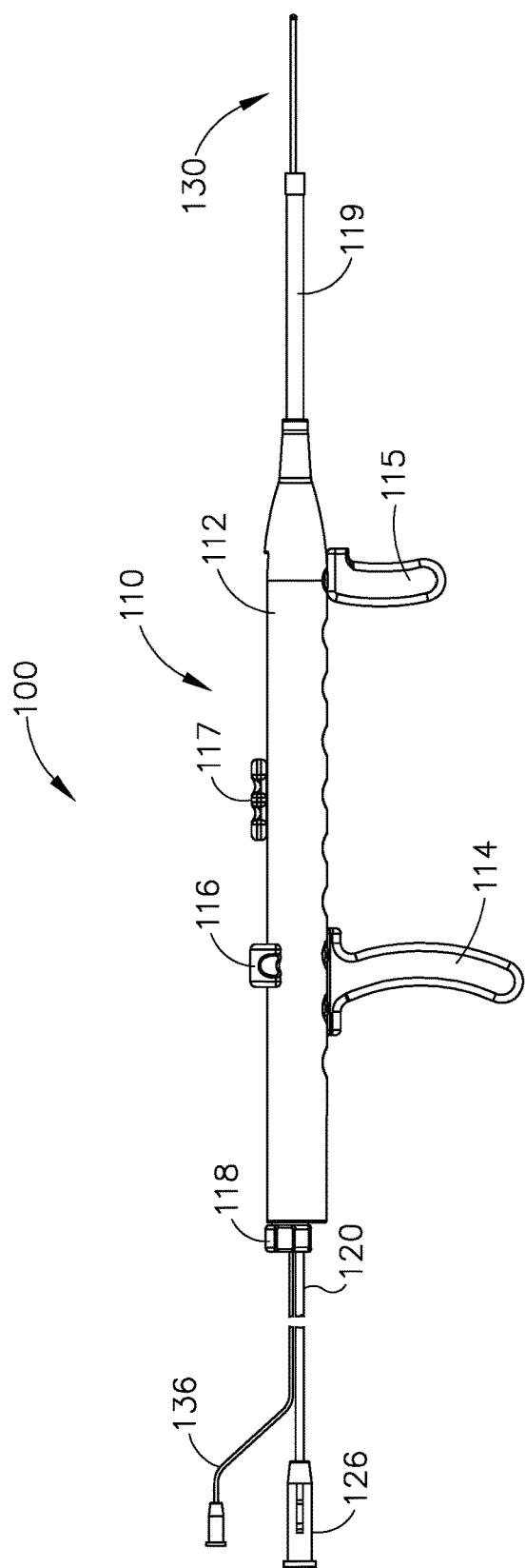
FIG. 6 depicts a side elevational view of an exemplary alternative dilation catheter system.

FIG. 6 shows an exemplary alternative dilation catheter system (110). Dilation instrument (100) comprises a handle assembly (110), a dilation catheter (120) (as can best be seen extending from handle assembly (110) in FIG. 19), and a guide assembly (130). Handle assembly (110) comprises a body (112), two adjustable grips (114, 115), two advancement sliders (116, 117), an open proximal end (118) and a rigid, hollow elongate cannula (119) extending distally from body (112). Handle assembly (110) is generally configured for manipulation by an operator such that guide assembly (130) may be inserted near a targeted anatomical passageway such as a sinus ostium as will be described in greater detail below.

Although not shown, it should be understood that body (112) includes a slot or other opening extending longitudinally across the upper portion of body (112). Such a slot is configured to permit longitudinal translation of sliders (116, 117) relative to body (112) to thereby advance a portion of guide assembly (130) and dilation catheter (120) as will be described in greater detail below.

Figure 7:
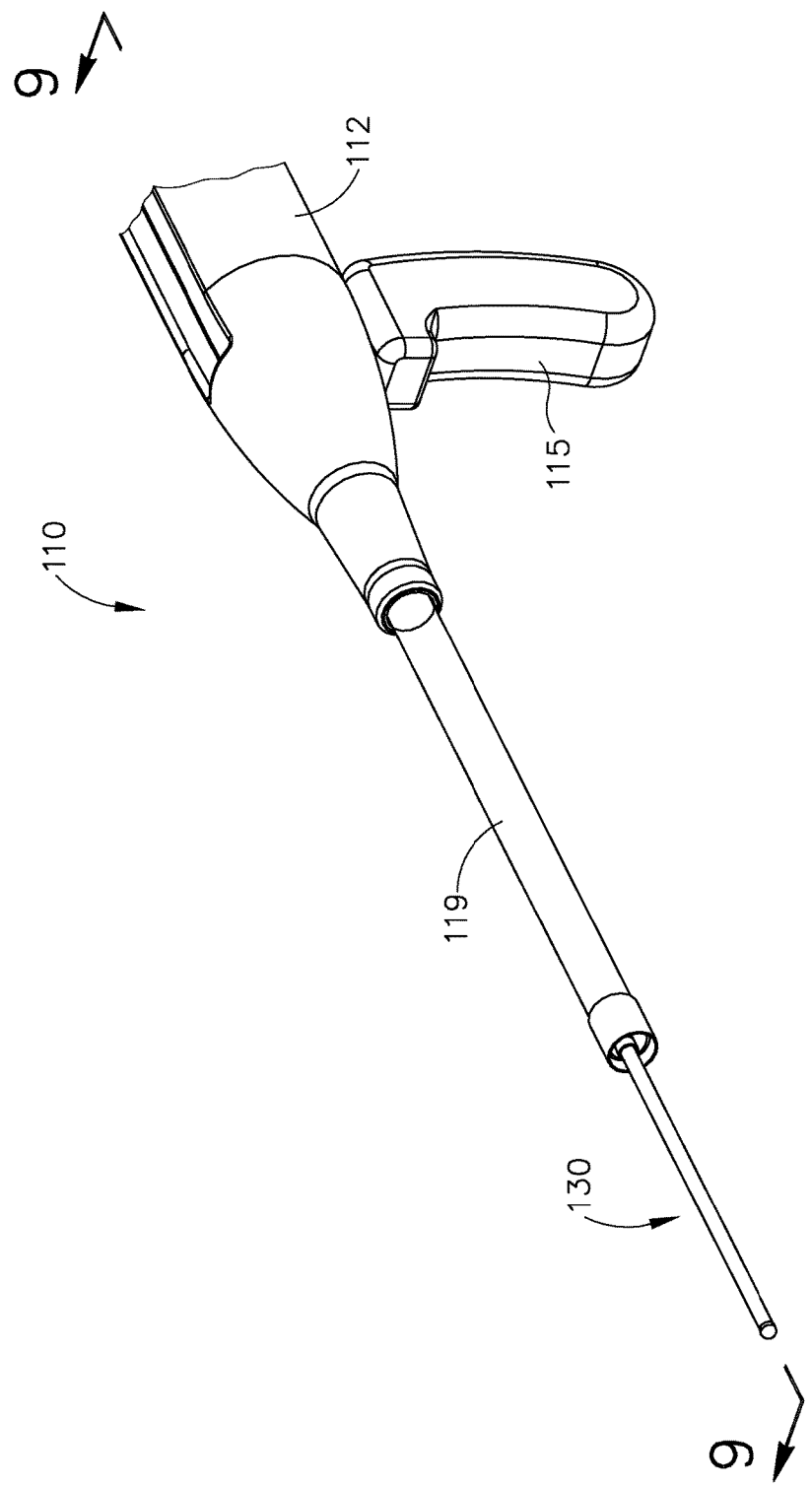
FIG. 7 depicts a perspective view of a guide assembly of the dilation catheter system of FIG. 6.
Figure 19:
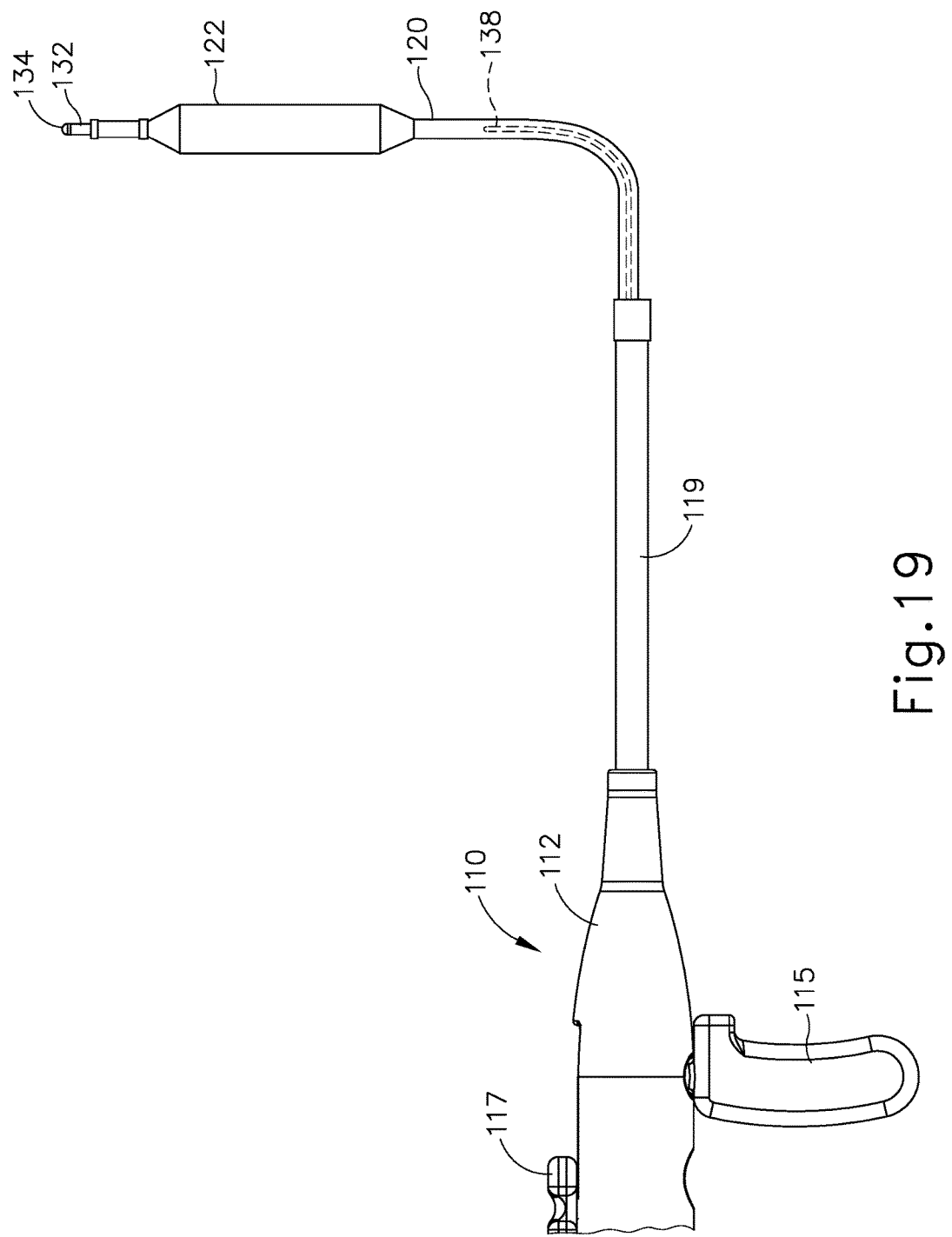
FIG. 19 depicts yet another side elevational view of the guide assembly of FIG. 7, with an inflatable dilator of the dilation catheter in an advanced and expanded configuration.
Figure 20:
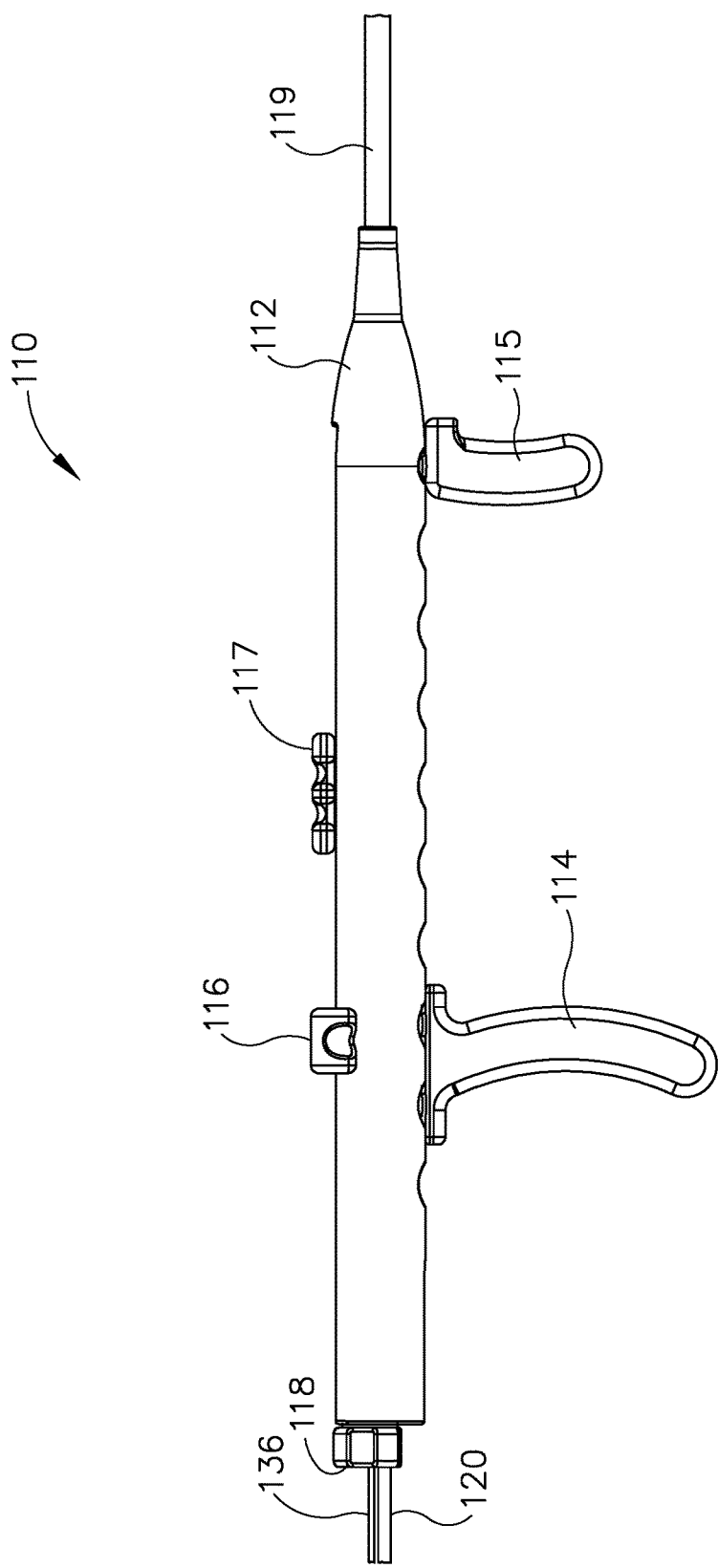
FIG. 20 depicts a side elevational view of a handle assembly of the dilation catheter system of FIG. 6.
Figure 21:
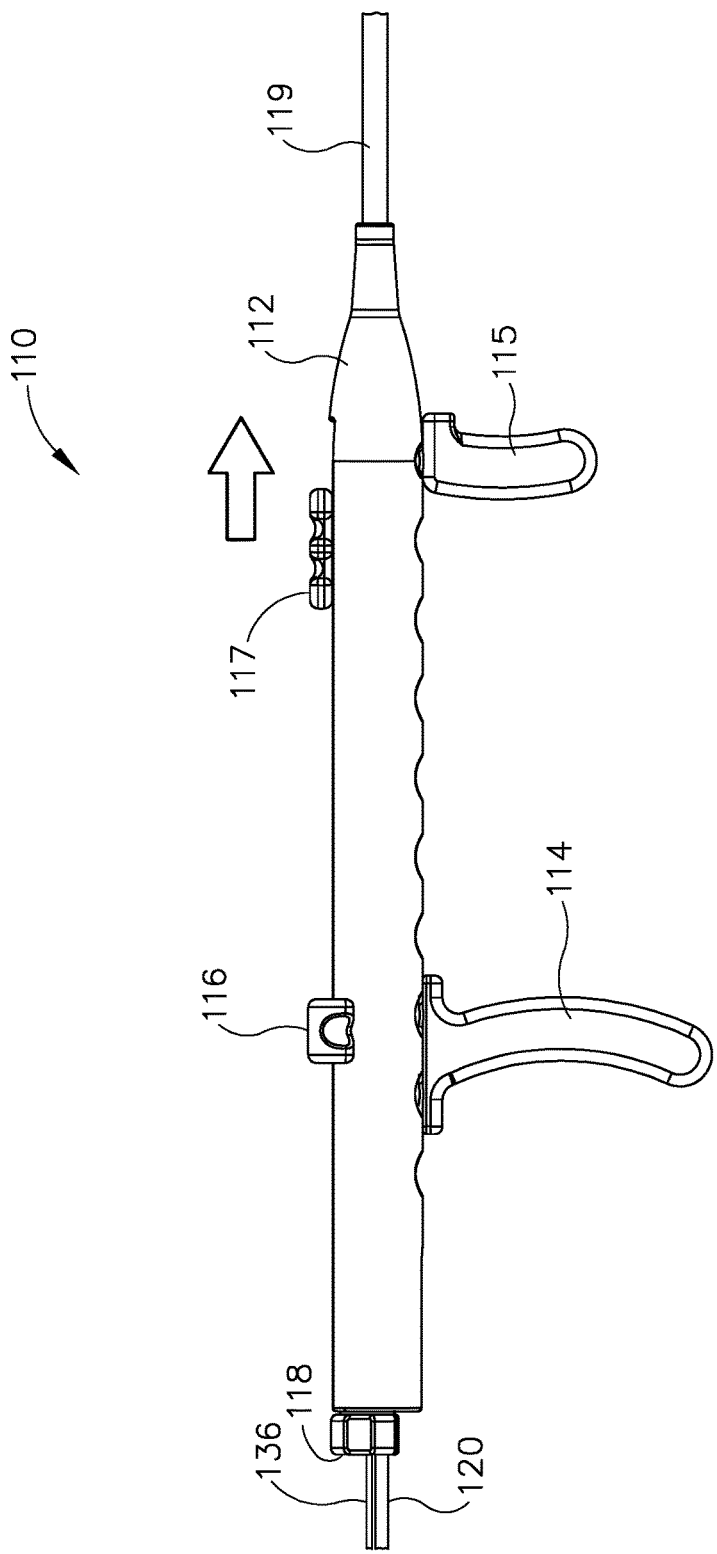
FIG. 21 depicts another side elevational view of the handle assembly of FIG. 20, with a guide slider advanced to a distal position.
Figure 22:
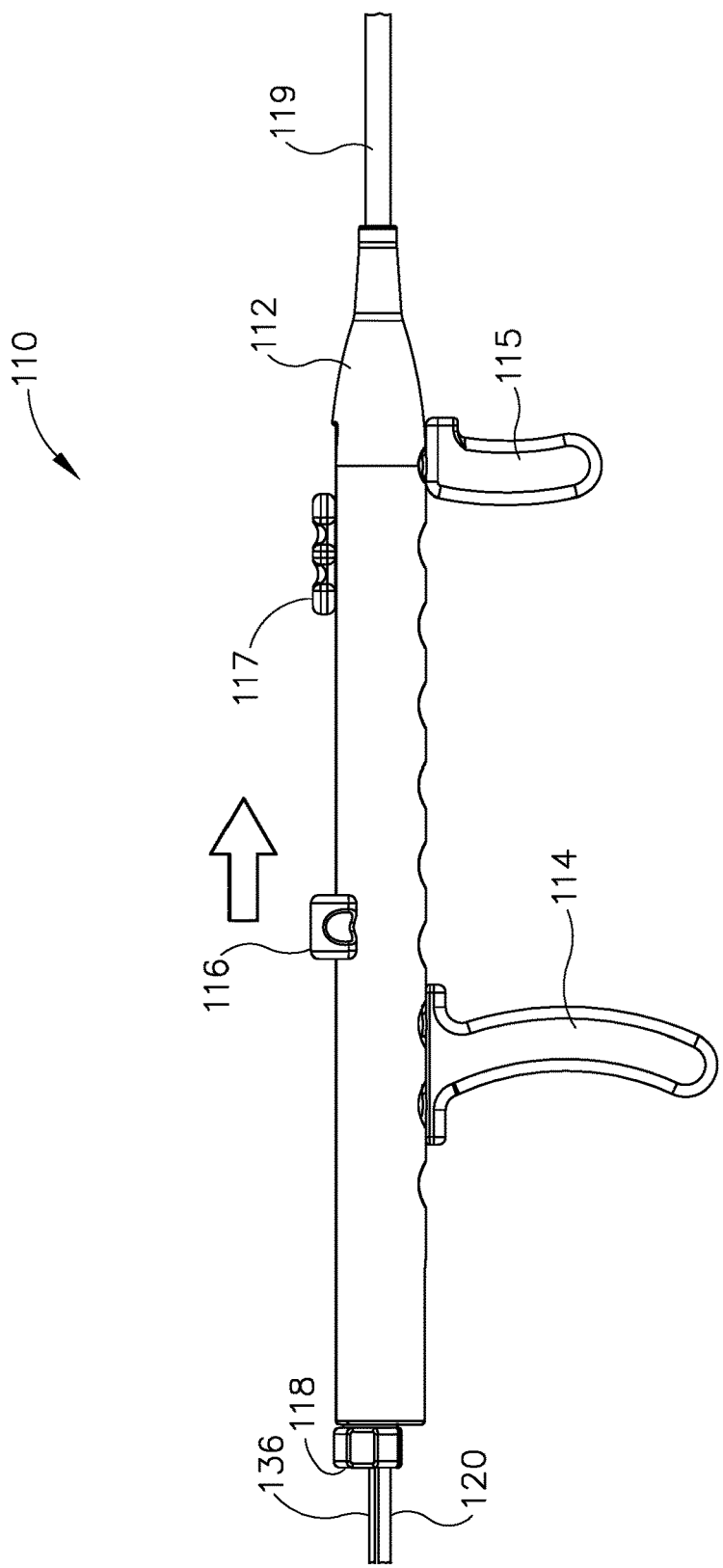
FIG. 22 depicts still another side elevational view of the handle assembly of FIG. 20, with a dilation catheter slider advanced to an intermediate position.
Figure 23:
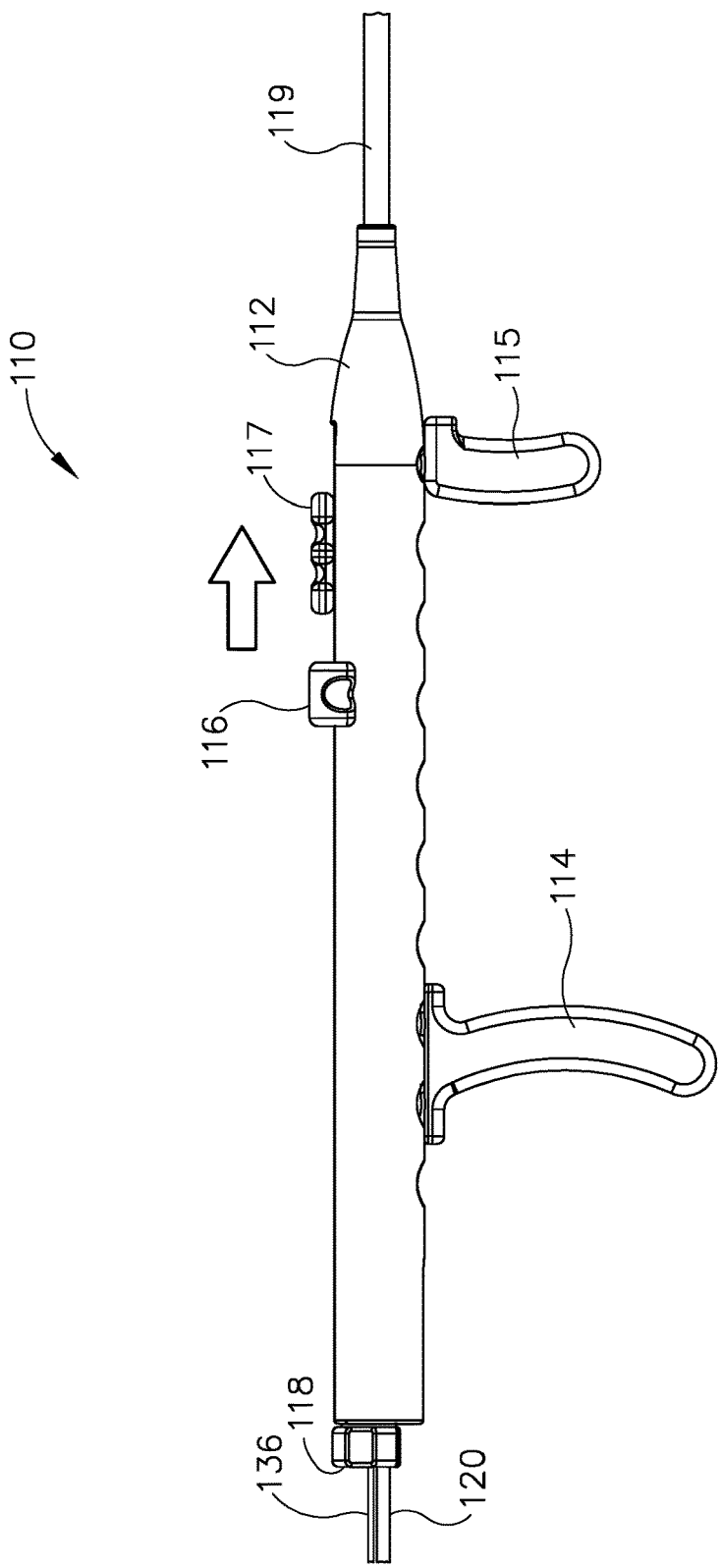
FIG. 23 depicts yet another side elevational view of the handle assembly of FIG. 20, with the dilation catheter slider advanced to a distal position.

Dilation catheter (120) is similar to dilation catheter (20) described above. For instance, the distal end of dilation catheter (120) includes an inflatable dilator (122) (as best seen in FIG. 19). The proximal end of dilation catheter (120) includes a port (126), which may be connected to an inflator (not shown) similar to inflator (40) described above to selectively inflate and deflate dilator (122). Dilation catheter (120) includes a first lumen (not shown) that provides fluid communication between port (126) and the interior of dilator (122). Dilation catheter (120) also includes a second lumen (not shown) that extends from the proximal end of dilation catheter (120) to an open distal end that is distal to dilator (122). This second lumen is configured to slidably receive guidewire (132). The first and second lumens of dilation catheter (120) are fluidly isolated from each other. Thus, dilator (122) may be selectively inflated and deflated by communicating fluid along the first lumen via port (126) while guidewire (132) is positioned within the second lumen. In some versions, dilation catheter (120) is configured similar to the Relieva Ultirra™ Sinus Balloon Catheter by Acclarent, Inc. of Menlo Park, Calif. In some other versions, dilation catheter (120) is configured similar to the Relieva Solo Pro™ Sinus Balloon Catheter by Acclarent, Inc. of Menlo Park, Calif. Other suitable forms that dilation catheter (120) may take will be apparent to those of ordinary skill in the art in view of the teachings herein As can be seen in FIG. 7, guide assembly (130) extends longitudinally through cannula (119) and out of a distal end thereof. As will be described in greater detail below, at least a portion of guide assembly (130) is slidable relative to cannula (119) such that distal advancement of guide advancement slider (117) results in advancement of at least a portion of guide assembly (130) distally relative to cannula (119). As will also be described in greater detail below, at least a portion of guide assembly (130) is malleable or otherwise deformable such that guide assembly (130) may be bent to a variety of positions suitable for accessing a targeted anatomical passageway such as a sinus ostium, the frontal recess, a Eustachian tube, or any other targeted anatomical passageway in the ear, nose, or throat.

Figure 8:
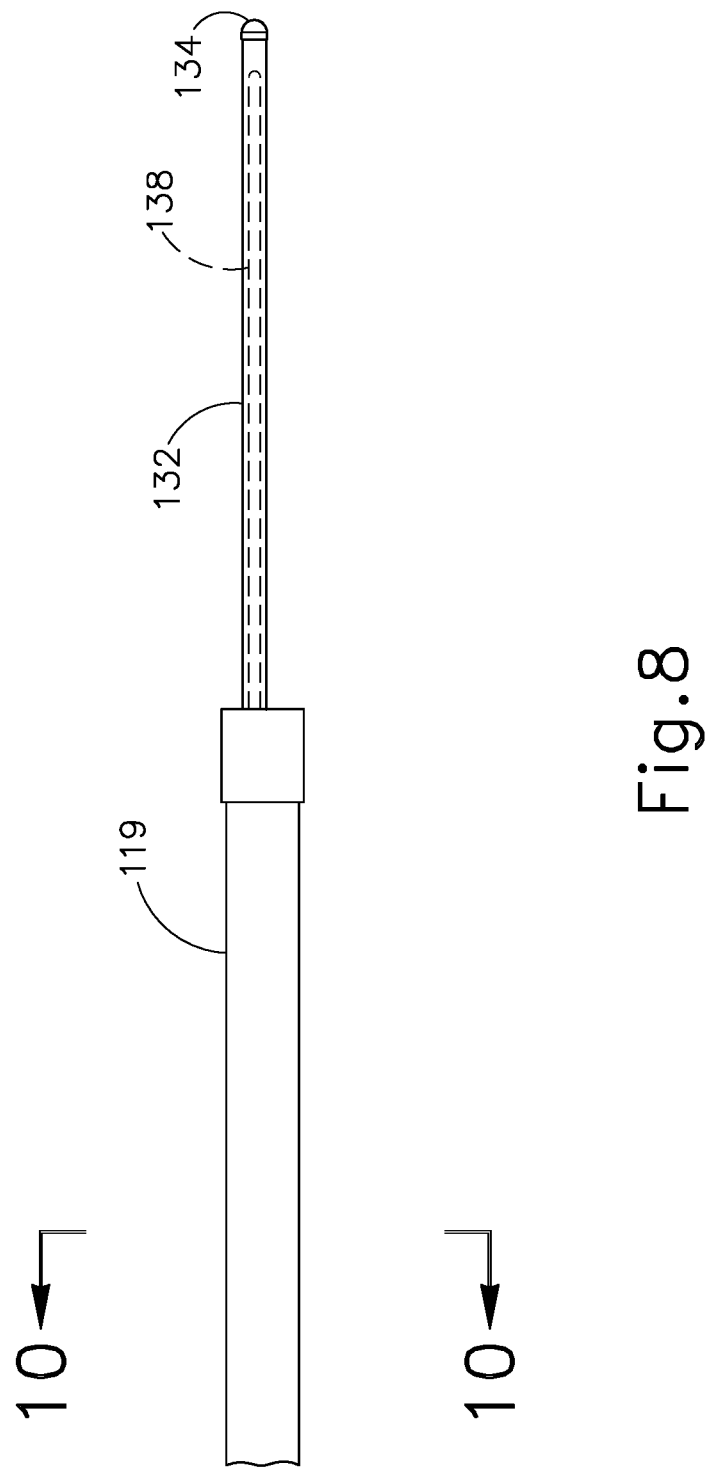
FIG. 8 depicts a side elevational view of the guide assembly of FIG. 7, with a guide rail shown in phantom.
Figure 9:
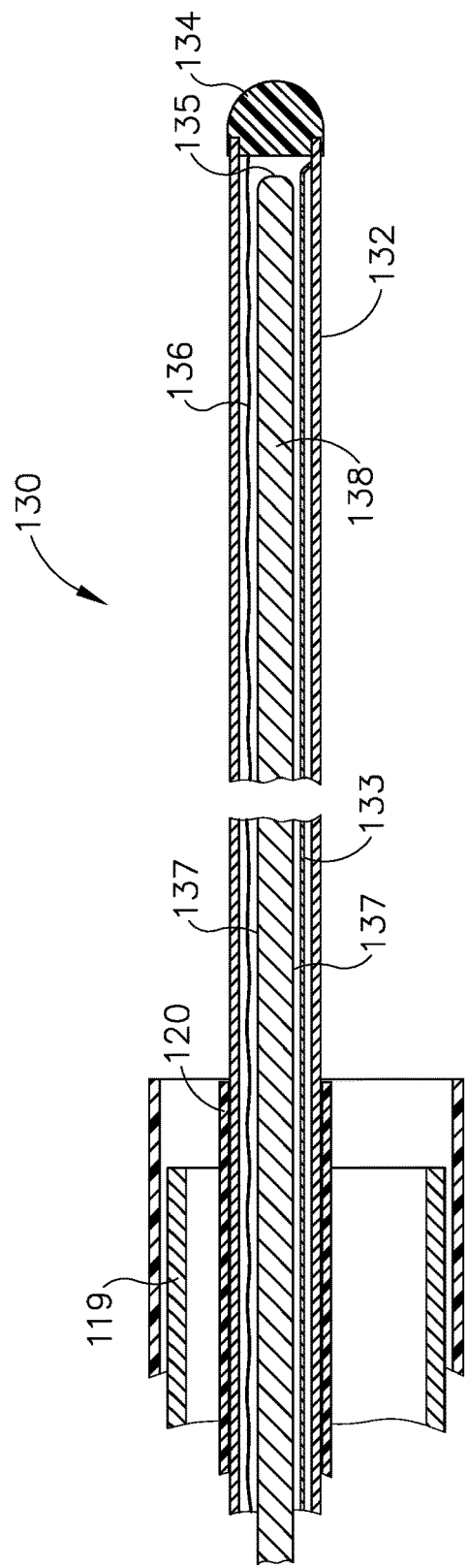
FIG. 9 depicts a side cross-sectional view of the guide assembly of FIG. 7, with the cross-section taken along line 9-9 of FIG. 7.
Figure 10:
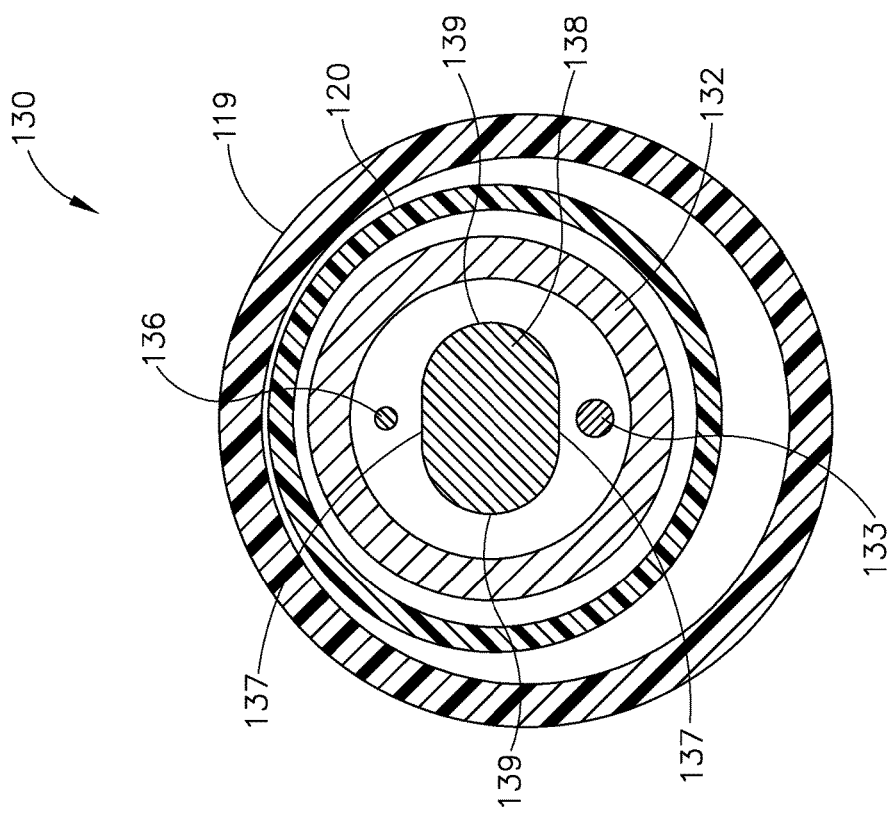
FIG. 10 depicts a front cross-sectional view of the guide assembly of FIG. 7, with the cross-section taken along line 10-10 of FIG. 8.

FIGS. 8-10 show detailed view of guide assembly (130). As can be seen, guide assembly (130) comprises an external guidewire (132) and an internal guide rail (138). Guidewire (132) is slidably disposed about guide rail (138). Guidewire (132) is generally flexible such that guidewire (132) may bendably navigate through a targeted anatomical passageway. Guidewire (132) generally comprises a coil of metal wire, such as stainless steel (e.g., SAE 304 stainless steel, SAE 316 stainless steel, nitinol, etc.). Alternatively, any other suitable metal(s) and/or other material(s) may be used. In the present example, the metal wire that is used to form guidewire (132) has a circular cross-sectional profile with a diameter between approximately 0.006 inches and approximately 0.007 inches. Alternatively, any other suitable wire gauge may be used. It should also be understood that the wire that is used to form guidewire (132) may alternatively have a flattened cross-sectional profile. As yet another merely illustrative alternative, guidewire (132) may have a woven construction instead of a coiled construction. In the present example, the metal wire forming guidewire (132) is wound in the form of a coil having an outer diameter between approximately 0.045 inches and approximately 0.060 inches, or more particularly approximately 0.052 inches. Alternatively, guidewire (132) may have any other suitable outer diameter.

While guidewire (132) of the present example is formed of metal, it should be understood that other suitable materials may be used. For instance, guidewire (132) may be formed as a polymeric extrusion. Exemplary plastics that may be used to form guidewire (132) include polyamide, polyether block amide (PEBAX), polydimethyl siloxane (silicone), etc. It should be understood that in examples where plastic materials are used, guidewire (132) may also provide enough optical transmissivity to enable visualization of guide rail (138) through the sidewall of guidewire (132). In versions where guide rail (138) is reflective, the reflectivity of guide rail (138) may further promote visualization of guide rail (138) through the side wall of guidewire (132). It should be further understood that in examples using plastic materials to form guidewire (132), a wire or polymer fiber having an open-stack or open braid configuration may be used to reinforce guidewire (132). Such a reinforcement feature may be configured to provide visibility of external guide rail (138) through the interstices of the coil or braid. In versions having an illuminating fiber (136) as described below, a glow emitted by illuminating fiber (136) may further distinguish the distal tip (135) of guide rail (138).

As another merely illustrative example, guidewire (132) may comprise a combination of a polymer extrusion and a metal coil. For instance, the proximal portion of guidewire (132) may comprise a polymer extrusion while the distal portion of guidewire (132) may comprise a metal coil that is joined with the polymer extrusion. The metal coil at the distal end may provide substantial flexibility, which may in turn provide greater atraumaticity to guidewire (132). Other suitable ways in which guidewire (132) may be formed will be apparent to those of ordinary skill in the art in view of the teachings herein.

As best seen in FIG. 9, guidewire (132) includes an atraumatic lens (134) affixed to the distal end of guidewire (132). Lens (134) is similar to lens (58) described above. Lens (134) is affixed to the distal end of guidewire (132) by any suitable means such as adhesive bonding, soldering, interference fitting, etc. In some versions, lens (134) is formed by an adhesive that is applied to the distal end of guidewire (132) and then allowed to cure. The adhesive material is optically transmissive such that the lens (134) formed of adhesive material is capable of transmitting light. Other suitable ways in which lens (134) may be formed will be apparent to those of ordinary skill in the art in view of the teachings herein. It should also be understood that lens (134) may have any suitable shape. For instance, lens (134) has a dome shape in the present example. In some other versions, lens (134) is shaped like a ball or a blueberry (e.g., as disclosed in U.S. Patent Pub. No. 2013/0274715, entitled "Method and System for Eustachian Tube Dilation," published on Oct. 17, 2013, now abandoned, the disclosure of which is incorporated by reference herein). Still other suitable shapes and configurations that lens (134) may have will be apparent to those of ordinary skill in the art in view of the teachings herein.

As shown in FIGS. 9-10, an illuminating fiber (136) extends longitudinally through guidewire (132) and is in optical communication with lens (134). Illuminating fiber (136) is parallel to the longitudinal axis of guidewire (132) but is laterally offset from the longitudinal axis of guidewire (132). It should be understood that illuminating fiber (136) extends through guidewire (132) into body (112) of handle assembly (110) and out of open proximal end (118) (as shown in FIG. 6) such that illuminating fiber (136) may be connected to a light source (not shown). Like with lens (58), lens (134) is configured to project light when illumination fiber (136) is illuminated by the light source, such that illumination fiber (136) transmits light from the light source to the lens (134). While only one illumination fiber (136) is shown, it should be understood that two or more illumination fibers (136) may be integrated into guidewire (132).

As also shown in FIGS. 9-10, guidewire (132) of the present example further comprises a core wire (133). Core wire (133) provides additional structural integrity to guidewire (132). Core wire (133) comprises a strand of nitinol that is secured to the proximal and distal ends of guidewire (132) through soldering or welding. In some versions, the diameter of core wire (133) is between approximately 0.008 inches and approximately 0.016 inches. Alternatively, any other suitable dimensions may be used.

As will be described in greater detail below, guidewire (132) is generally configured for advancement over guide rail (138) such that guidewire (132) may be advanced while guide rail (138) remains stationary. As will also be described below, guidewire (132) is also configured such that dilation catheter (120) may be advanced over guidewire (132). Accordingly, in some versions, guidewire (132) includes a coating such as polytetrafluoroethylene (PTFE), silicone, or some other kind of coating that facilitates advancement of dilation catheter (120) along guidewire (132), particularly when guidewire (132) is bent to provide a non-linear path for translation of dilation catheter (120). Where such a coating is utilized, guidewire (132) may be coated on the both the exterior and the interior of guidewire (132), or on either the interior or the exterior of guidewire (132). Of course, such a coating is merely optional and in some examples guidewire (132) is uncoated.

As can best be seen in FIGS. 9-10, guide rail (138) is generally shaped as an elongate solid rod having an ovular transverse cross-section and a rounded distal tip (135). By way of example only, the ovular cross-sectional profile of guide rail (138) may have a width between approximately 0.018 inches and approximately 0.034 inches; and a height between approximately 0.012 inches and approximately 0.026 inches. By way of further example only, the ovular cross-sectional profile of guide rail (138) may have a width of approximately 0.030 inches and a height of approximately 0.020 inches. Alternatively, any other suitable dimensions may be used.

While guide rail (138) of the present example has an ovular cross section, it should be understood that other cross sectional configurations may be used. By way of example only, guide rail (138) may have an elliptical cross sectional profile, a cross sectional profile formed by a rectangle with chamfered edges, or any other suitable cross sectional profile. In the present example, the ovular cross sectional profile of guide rail (138) presents broad opposing regions (137) and narrow opposing regions (139). Guide rail (138) of the present example comprises a solid metal wire. By way of example only, guide rail (138) may be formed of stainless steel (e.g., SAE 304 stainless steel, SAE 316 stainless steel, etc.) that as annealed or partially annealed. Other suitable materials that may be used to form guide rail (138) will be apparent to those of ordinary skill in the art in view of the teachings herein.

As described in greater detail below, guide rail (138) is bendable along a plane passing through broad opposing regions (137) but not along a plane passing through narrow opposing regions (139). In other words, guide rail (138) is bendable along just one single orthogonal plane in the present example. In some other versions, guide rail (138) is bendable along two orthogonal planes. For instance, some alternative versions of guide rail (138) may be bendable along a first plane passing through broad opposing regions (137) and along a second plane passing through narrow opposing regions (139). Some such versions of guide rail (138) may warrant a cross-sectional profile that is different from the ovular profile of guide rail (138) in the present example. In other words, in order to provide bending along two orthogonal planes, guide rail (138) may need to be reconfigured to have a cross-sectional profile that is circular, square, or of some other shape that facilitates bending along two orthogonal planes.

Guide rail (138) extends through guidewire (132) and is generally longitudinally fixed relative to handle assembly (110). Guide rail (138) thus does not translate relative to handle assembly (110). In some versions, however, guide rail (138) is rotatable relative to handle assembly (110). For instance, handle assembly (110) may comprise a knob, lever, spindle, or other input feature that provides rotation of guide rail (138) about the longitudinal axis of guide rail (138). In some such versions, guide rail (138) may be rotated after guide rail (138) has been bent to achieve a desired bend angle as described below.

It should be understood that with the combination of shape and materials described herein, guide rail (138) is malleable such that guide rail (138) may be deformed to various bend angles; and such that guide rail (138) may maintain such bend angles. As will be described in greater detail below, the malleability guide rail (138) permits an operator to manipulate guide rail (138) into a desired position to access a targeted anatomical passageway. Once guide rail (138) is bent, guidewire (132) and/or dilation catheter (120) is advanceable over guide rail (138) into position relative to the targeted anatomical passageway. Like with guidewire (132) described above, guide rail (138) may also be coated to increase the slidability of guidewire (132) relative to guide rail (138). For instance, guide rail (138) may be coated with polytetrafluoroethylene (PTFE) and/or any other suitable lubricious coating. It should be understood that while certain shapes and/or materials of guide rail (138) are described herein, in other examples guide rail (138) may comprise any other shape and/or material as will be apparent to those of ordinary skill in the art in view of the teachings herein.

Figure 11:
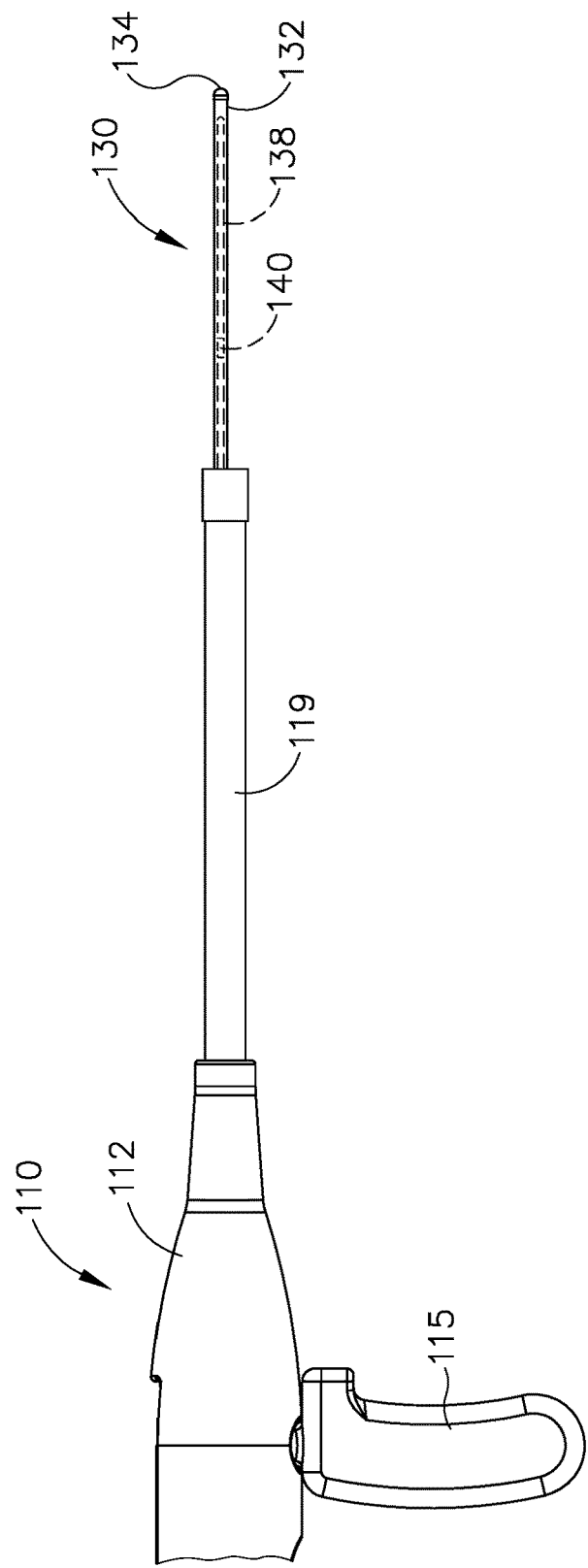
FIG. 11 depicts another side elevational view of the guide assembly of FIG. 7, with the guide assembly in a straight configuration.
Figure 12:
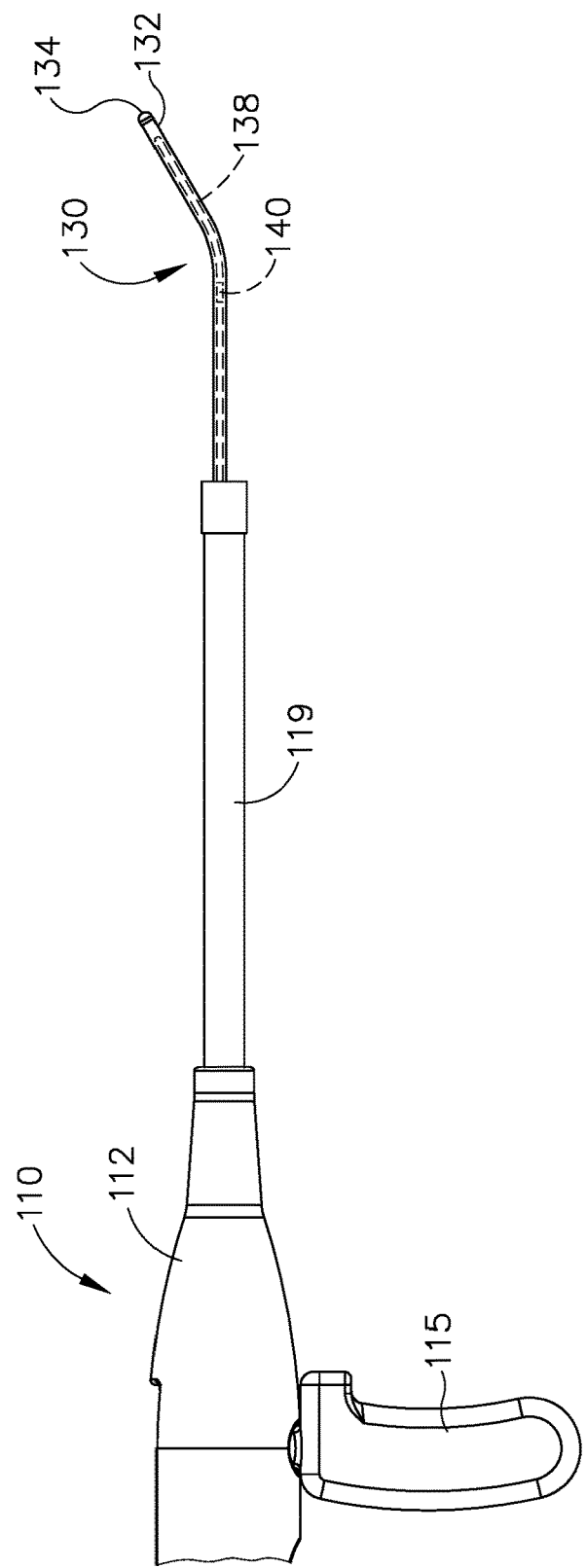
FIG. 12 depicts still another side elevational view of the guide assembly of FIG. 7, with the guide assembly having a 30° bent configuration.

FIGS. 11-15 show various configurations into which guide rail (138) of the present example may be deformed. For instance as can be seen in FIG. 11, guide rail (138) may be used in a straight configuration without any deformation at all. When guide rail (138) is in the straight configuration, guide assembly (130) may be useable to access an ostium (O) of a sphenoid sinus. In other examples, guide rail (138) may be deformed into a curve having an angle of about 30° relative to the longitudinal axis of guide assembly (130) as shown in FIG. 12. When guide rail (138) is in the 30° configuration, guide assembly (130) may also be generally usable for also accessing an ostium (O) of a sphenoid sinus.

Figure 13:
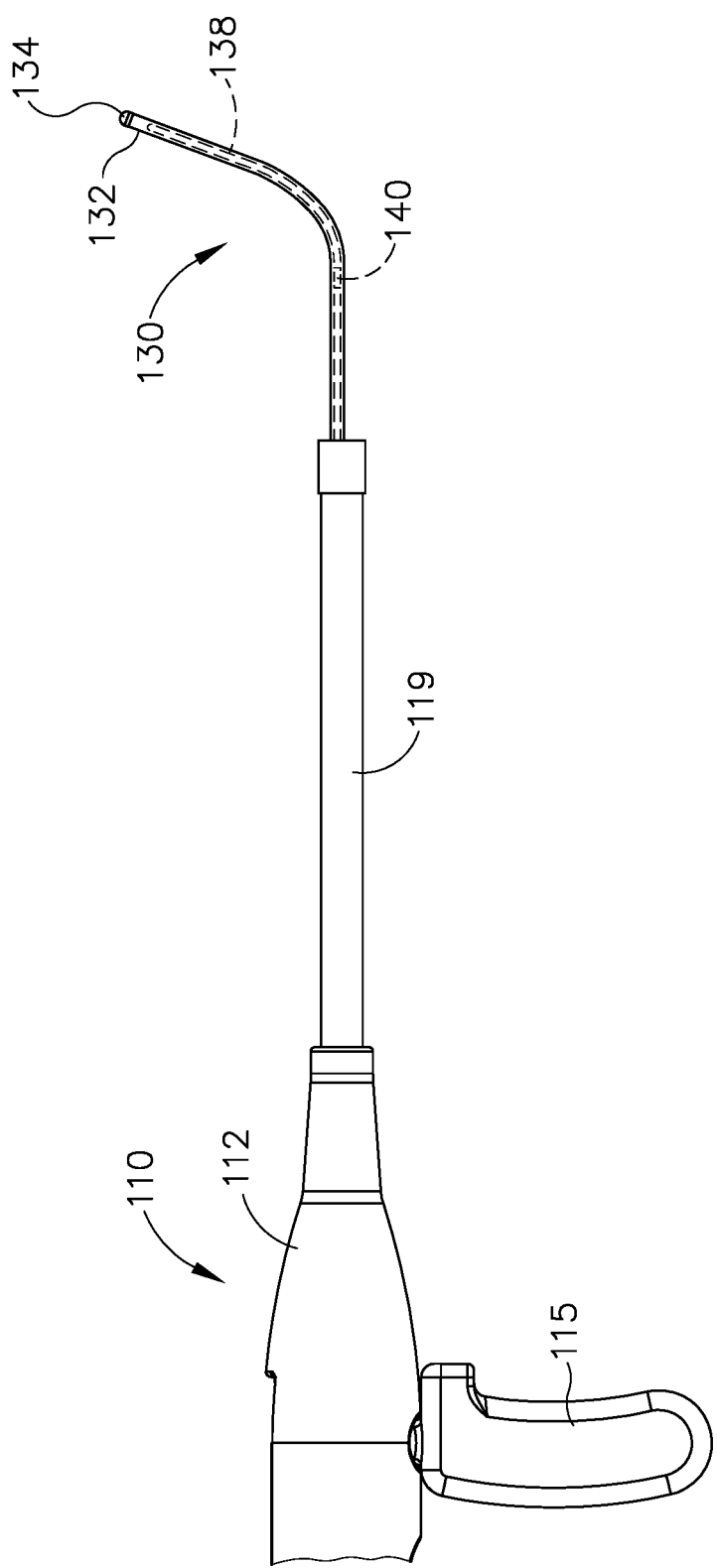
FIG. 13 depicts yet another side elevational view of the guide assembly of FIG. 7, with the guide assembly having a 70° bent configuration.

As can be seen in FIG. 13, guide rail (138) is also deformable into a curve angle of about 70° relative to the longitudinal axis of guide assembly (130). When guide rail (138) is in the 70° configuration, guide assembly (130) is generally usable for accessing the frontal recess associated with a frontal sinus.

Figure 14:
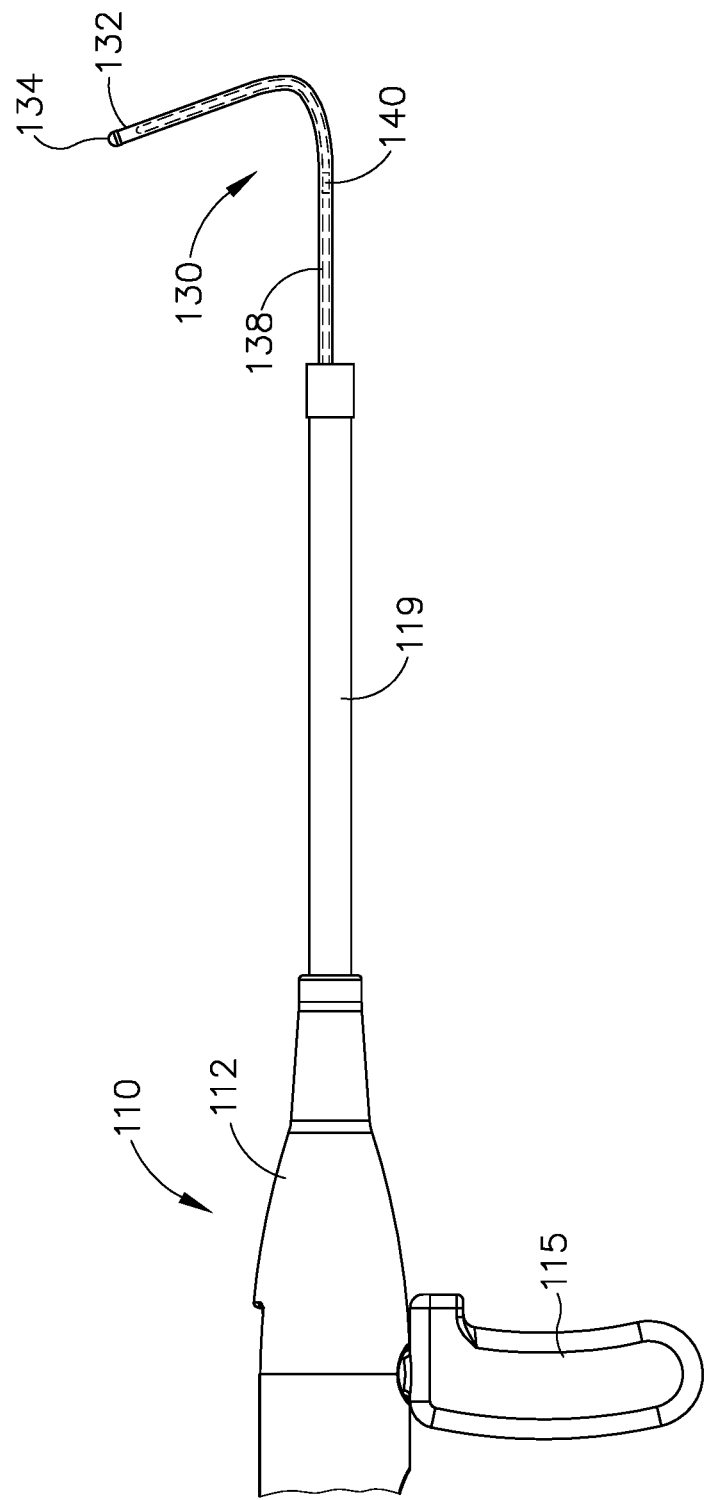
FIG. 14 depicts a yet another side elevational view of the guide assembly of FIG. 7, with the guide assembly having a 110° bent configuration.

As can be seen in FIG. 14, guide rail (138) is further deformable into a curve angle of about 110° relative to the longitudinal axis of guide assembly (130). When guide rail (138) is in the 110° configuration, guide assembly (130) is generally usable for accessing an ostium (O) of a maxillary sinus without requiring surgical removal or mitigation of the uncinate process. It should be understood that guide rail (138) may be bent to various different angles to facilitate access to the ostium (O) of a maxillary sinus, including but not limited to any suitable angle within the range of approximately 110° to approximately 130°. It should also be understood that the bend angle may be formed at a location that is further distal along the length of guide rail (138) than the position shown in FIG. 14 in order to promote access to the ostium (O) of a maxillary sinus. For instance, when guide rail (138) is bent to provide access to the ostium (O) of a maxillary sinus, the bend may be formed approximately 10 mm proximal to distal tip (135) of guide rail (138). Positioning the bend at such a longitudinal position may facilitate positioning of distal end of guide assembly (130) around the uncinate process in order to access the ostium (O) of the maxillary sinus.

Figure 15:
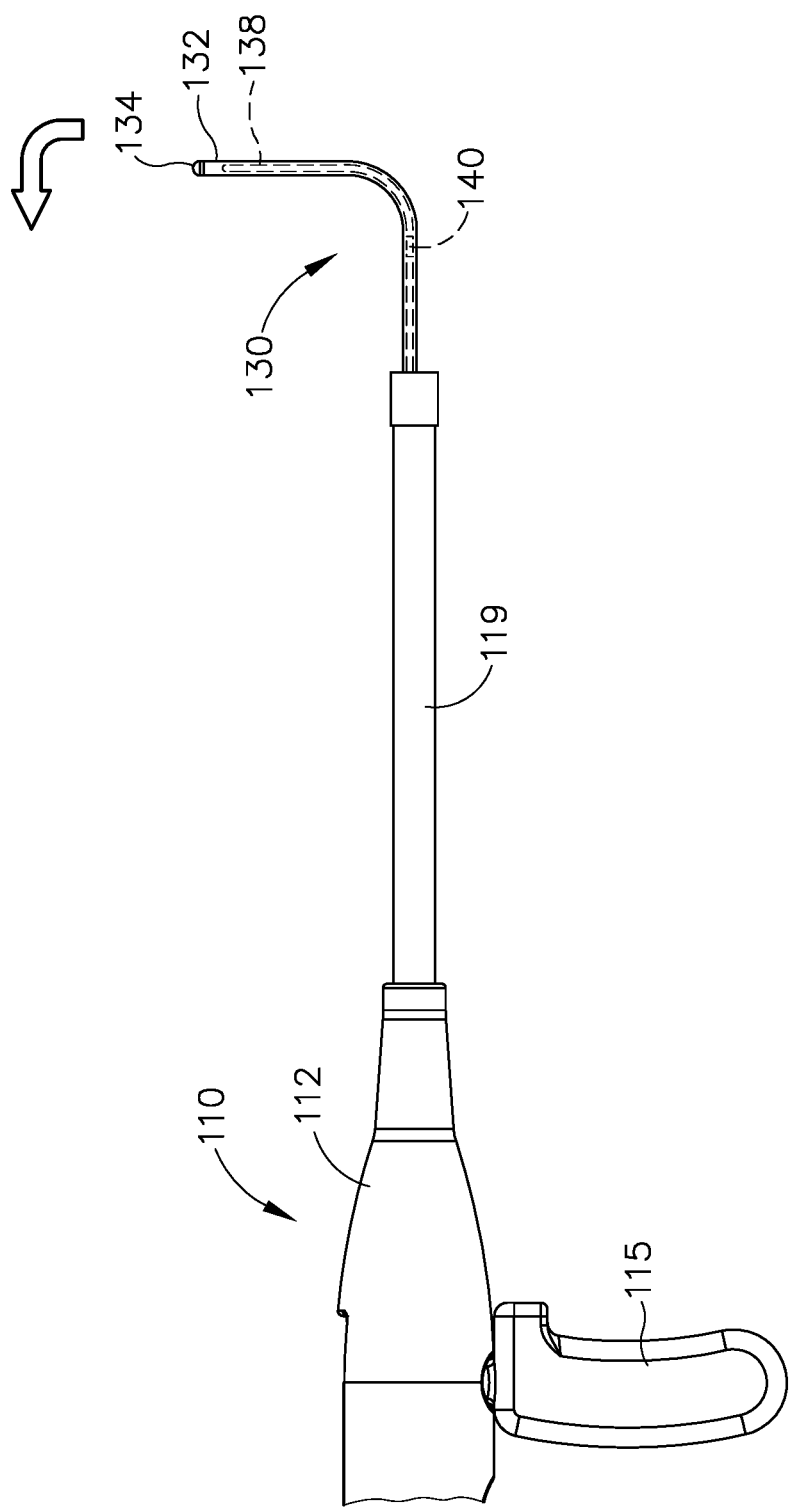
FIG. 15 depicts a yet another side elevational view of the guide assembly of FIG. 7, with the guide assembly having a 90° bent configuration.
Figure 16:
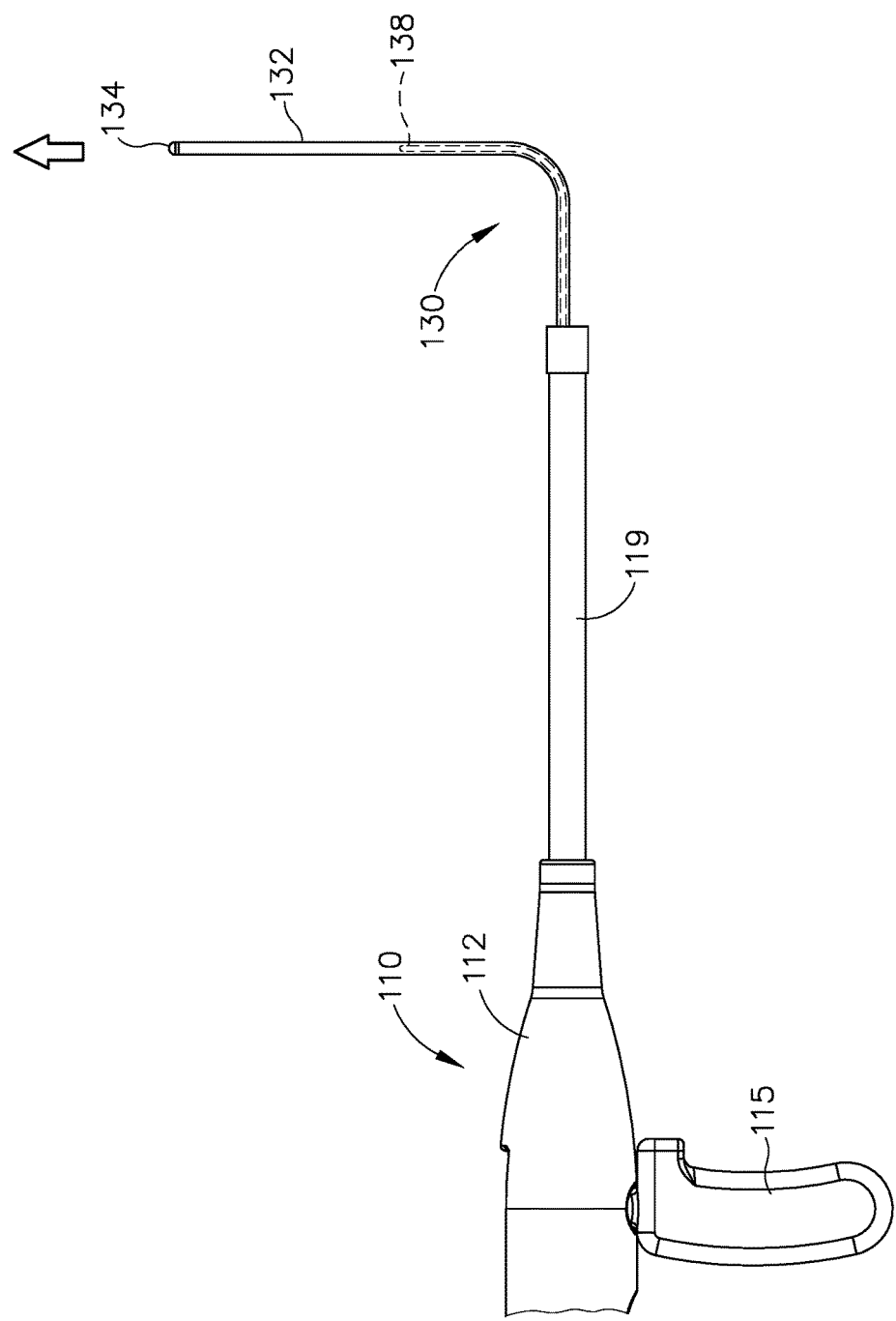
FIG. 16 depicts yet another side elevational view of the guide assembly of FIG. 7, with a guidewire of the guide assembly in a partially advanced configuration.

As can be seen in FIG. 15, guide rail (138) is further deformable into a curve angle of about 90° relative to the longitudinal axis of guide assembly (130). When guide rail (138) is in the 90° configuration, guide assembly (130) is generally usable for accessing an ostium (O) of maxillary sinuses and in some cases a frontal recess. As another merely illustrative example, guide rail (138) may be deformed to facilitate orientation of guide rail (130) toward a pharyngeal ostium of a Eustachian tube. For instance, in order to facilitate orientation of guide rail (130) toward a pharyngeal ostium of a Eustachian tube, guide rail (138) may be bent to achieve a bend angle between approximately 45° and approximately 65°, or more particularly between approximately 50° and approximately 60°, or more particularly approximately 55°. Alternatively, guide rail (138) may be deformed to any other suitable bend angles as will be apparent to those of ordinary skill in the art in view of the teachings herein.

In the present example, guide assembly (130) is bent by grasping handle assembly (110) with one hand, grasping guide assembly (130) with the other hand (at a longitudinal position associated with the distal region of guide rail (138)), and then using both hands to manually bend guide assembly. As shown schematically in FIGS. 11-15, guide rail (138) may include angle stops (140) or other mechanical features to provide a tactile indication to an operator when guide rail (138) has been positioned in a given angle. For instance, such angle stops (140) may be configured to provide indications at bend angles of approximately 0°, 30°, 55°, 70°, 90°, 110°, and/or 130°. In addition to or as an alternative to such angle stops (140), a separate bending tool or template may be used to bend guide rail (138) to specific predetermined bend angles. For instance, such a tool or template may provide a visual indication of certain bend angles, such that the operator may visually compare the bend angle of guide rail (138) to a desired bend angle shown on the template until the desired bend angle is achieved. Alternatively, the tool or template may include channels or other features that are configured to receive guide rail (138), such that the operator may bend guide rail (138) in or on such features in order to achieve the desired bend angle. Other suitable ways in which bending tools or templates may be configured and used will be apparent to those of ordinary skill in the art in view of the teachings herein.

As another merely illustrative example, guide rail (138) may be steerable. For instance, handle assembly (110) may include a user input feature such as a slider, knob, lever, etc. that is operable to selectively adjust the bend angle of guide rail (138). The user input feature may be coupled with one or more cables, bands, or other features that are further coupled with guide rail (138) and that are operable to selectively deform guide rail (138). For instance, such features may be configured similar to steering features that are found in conventional steerable endoscopes. Alternatively, such features may be configured similar to articulation drive features that are found in conventional articulating surgical instruments. Various suitable ways in which guide rail (138) may be steered or otherwise deformed through a user input feature in handle assembly (110) will be apparent to those of ordinary skill in the art in view of the teachings herein.

In some variations, guidewire (132) includes a visual indicator (e.g., a stripe, etc.) along a region associated with one of the broad regions (137) of guide rail (138). Such an indicator may enable the operator to more readily determine the location of the inside of the bend formed by guide assembly (130), particularly when the bent region of guide assembly (130) is positioned within the nasal cavity of the patient. For instance, the operator may visualize the indicator using endoscope (60) or any other suitable visualization means.

FIGS. 11 and 15-23 show an exemplary use of dilation instrument (100). As can be seen in FIG. 11, guide assembly (130) initially begins in the straight configuration such that guide rail (138) is substantially undeformed. An operator may next deform guide rail (138) to a desired position to configure guide assembly (130) for a particular targeted anatomical passageway. As noted above, FIGS. 12-14 show a few merely illustrative bend angles that may be readily achieved by guide assembly (130). FIG. 15 shows guide assembly (130) having a bend angle of approximately 90°, though this is of course just one other merely illustrative example.

Once guide rail (138) is deformed into a desired position to configure guide assembly (130) for a particular targeted anatomical passageway, the operator may position instrument (100) to direct guide assembly (130) into position within a patient. For instance, in some examples this may include an operator inserting guide assembly (130) into a nostril of a patient. As guide assembly (130) is inserted into a patient, and while guidewire (132) is still in the proximal-most position as shown in FIG. 15, guide assembly (130) may be used as a probe or seeker to locate particular anatomical regions due to guide rail (138) providing at least some stiffness to guide assembly (130).

Once guide assembly (130) is suitably positioned and oriented within a patient, the operator may wish to advance guidewire (132) into or through the anatomical passageway that is intended to be dilated. To advance guidewire (132), the operator may advance guide slider (117) distally from the position shown in FIG. 20 to the position shown in FIG. 21. Advancement of guide slider (117) provides corresponding advancement of guidewire (132) over guide rail (138) to from the position shown in FIG. 16 to the position shown in FIG. 17. It should be understood that as guidewire (132) is advanced, guide rail (138) remains stationary, thereby maintaining the curve formed in guide rail (138) in a fixed position. Accordingly, the particular portion of guidewire (132) that is disposed over guide rail (138) remains relatively inflexible because of guide rail (138); while the particular portion of guidewire (132) advanced beyond guide rail (138) is relatively flexible. Guidewire (132) advances along a trajectory formed by bent guide rail (138). It should be understood that as guidewire (132) is advanced, such advancement of guidewire (132) may correspond to advancement through anatomy of a patient toward a targeted anatomical passageway of the patient.

Figure 17:
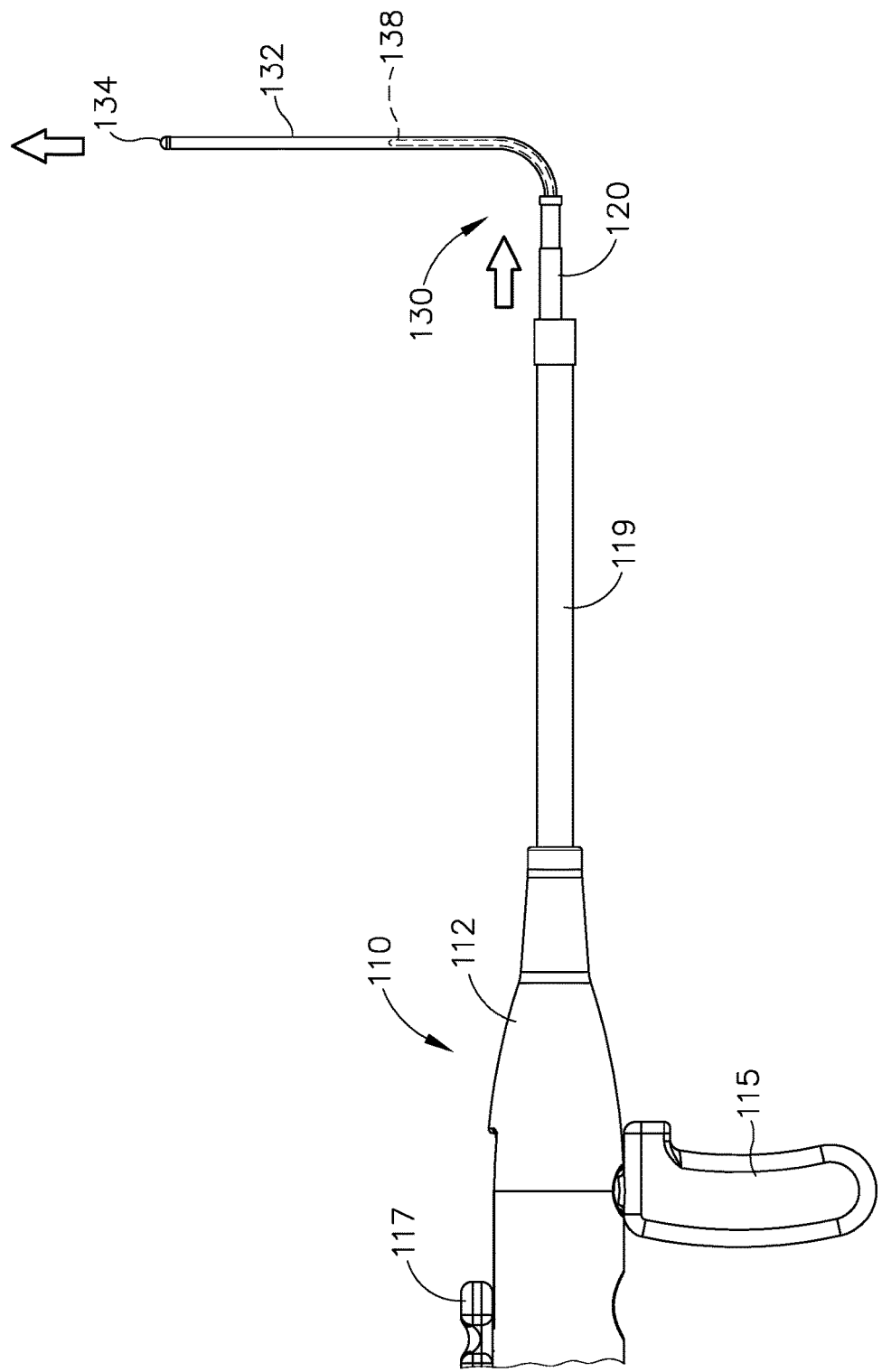
FIG. 17 depicts yet another side elevational view of the guide assembly of FIG. 7, with the guidewire of FIG. 16 in a fully advanced configuration and a dilation catheter partially advanced.
Figure 18:
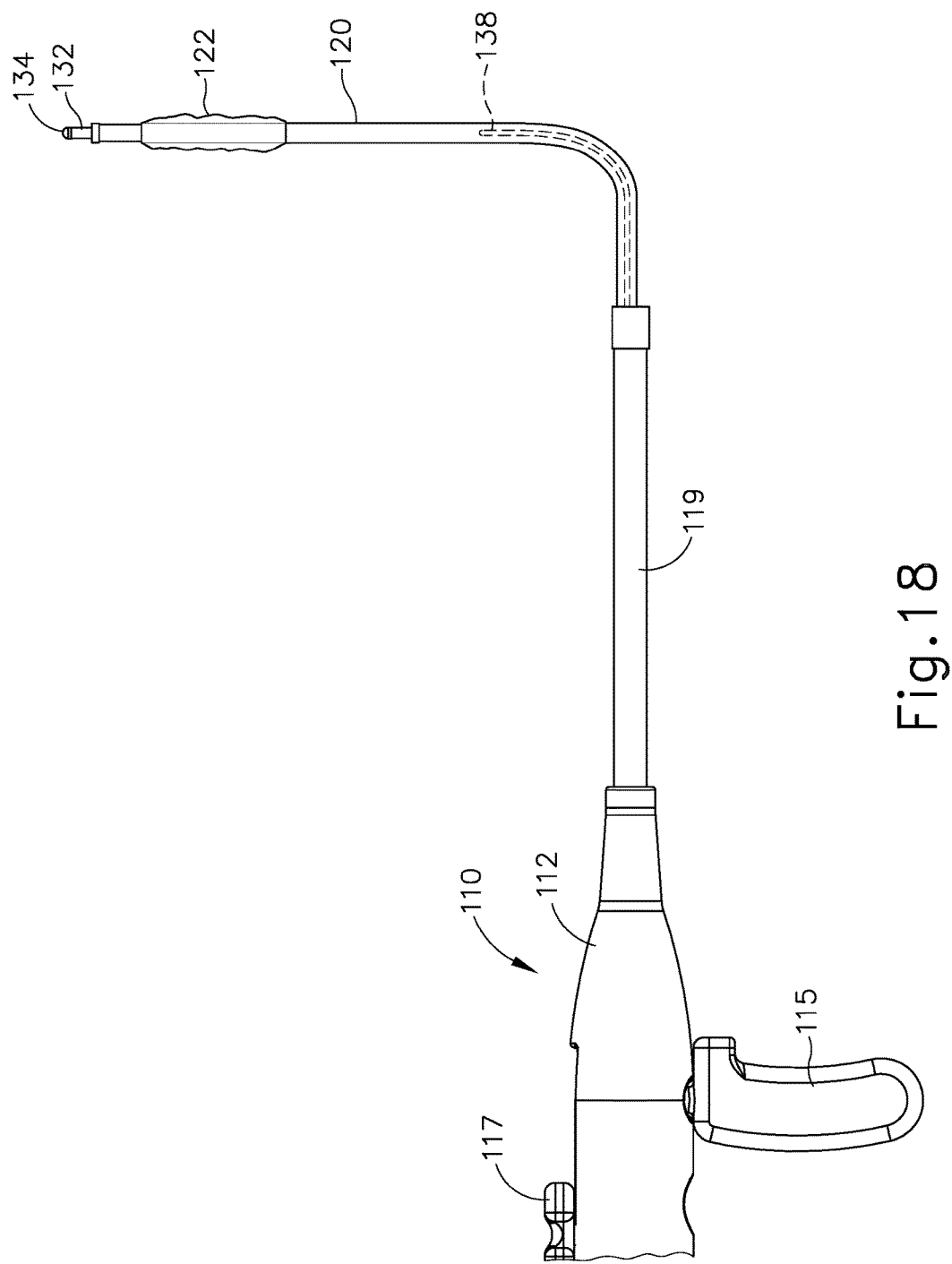
FIG. 18 depicts yet another side elevational view of the guide assembly of FIG. 7, with the guidewire and dilation catheter fully advanced.

Once guidewire (132) is advanced to a desired position relative to a targeted anatomical passageway, the operator may cease advancement of guidewire (132) and initiate advancement of dilation catheter (120). To initiate advancement of dilation catheter (120), the operator may advance a dilation catheter slider (116) from the position shown in FIG. 21 through the position shown in FIG. 22 and finally to the position shown in FIG. 23. When dilation catheter slider (116) is in the position shown in FIG. 21, dilation catheter (120) is correspondingly disposed within handle assembly (110). As dilation catheter slider (116) is advanced through the position shown in FIG. 22, dilation catheter (120) correspondingly advances out of cannula (119) of handle assembly (110) as shown in FIG. 17. As dilation catheter slider (116) is advanced to the position shown in FIG. 23, dilation catheter (120) correspondingly advances over guidewire (132) around the curve in guide rail (138) to the position shown in FIG. 18. Thus, like guidewire (132), dilation catheter (120) advances along a trajectory formed by bent guide rail (138). Dilation catheter (120) continues along the path provided by guidewire (132).

Once dilation catheter (120) is advanced to the position shown in FIG. 19, the operator may wish to expand dilator (122) of dilation catheter (120). It should be understood that when dilation catheter (120) is in the position shown in FIG. 19, such a position may correspond to dilator (122) being positioned a desired anatomical passage such as a sinus ostium, the frontal recess, etc. It should also be understood that the position shown in FIG. 19 is just an example. Distal advancement of dilator (122) may cease when dilator (122) has reached any other suitable position along the length of guidewire (132). Dilator (122) may thus be stopped and expanded while dilator (122) while dilator is at any suitable location proximal to the location shown in FIG. 19. To expand dilator (122), the operator may actuate the inflator as similarly described above with respect to dilation catheter (20). By way of example only, dilator (122) may be inflated to a volume sized to achieve about 10 to about 12 atmospheres. Dilator (122) may be held at this volume for a few seconds to sufficiently open the ostium (or other targeted anatomical passageway). Dilator (122) may then be returned to a non-expanded state by reversing the inflator to bring the saline back to the inflator. Dilator (122) may be repeatedly inflated and deflated in different ostia and/or other targeted anatomical passageways.

Thereafter, dilation catheter (120) and guide assembly (130) may be removed from the patient. Dilation catheter (120) may be retracted proximally along guide assembly (130), and then guidewire (132) retracted along guide rail (138), before instrument (100) is removed from the patient. It should be understood that dilation catheter (120) may slide relatively smoothly along guidewire (132) as dilation catheter (120) is retracted proximally along guide assembly (130). The positioning of guidewire (132) about guide rail (138), in combination of the rounded configuration of distal tip (135) of guide rail (138), may prevent dilation catheter (120) from getting snagged on any portion of guide assembly (130) as dilation catheter (120) is retracted proximally along guide assembly (130). Once dilation catheter (120) and guide assembly (130) are removed from the patient, the operator may optionally re-bend guide rail (138) for targeting of a different anatomical passageway and the procedure as described above may be repeated.

IV. Exemplary Alternative Guide Assemblies

In some instances it may be desirable to increase the stiffness of a guide assembly similar to guide assembly (130) described above. Such an increase in stiffness may desirable to permit the guide assembly to more readily navigate through tortuous anatomical features. Various alternative guide assemblies are described herein having features for increasing the stiffness of the guide assembly. It should be understood that these exemplary alternative guide assemblies may readily incorporate various features of dilation catheter system (10) and/or instrument (100) described above and may be additionally used with endoscope (60) described above. While certain alternative guide assemblies are described herein, other suitable configurations and arrangements will be apparent to those of ordinary skill in the art in view of the teachings herein.

A. Exemplary Alternative Guide Assembly with Stiffening Core Wire

Figure 24:
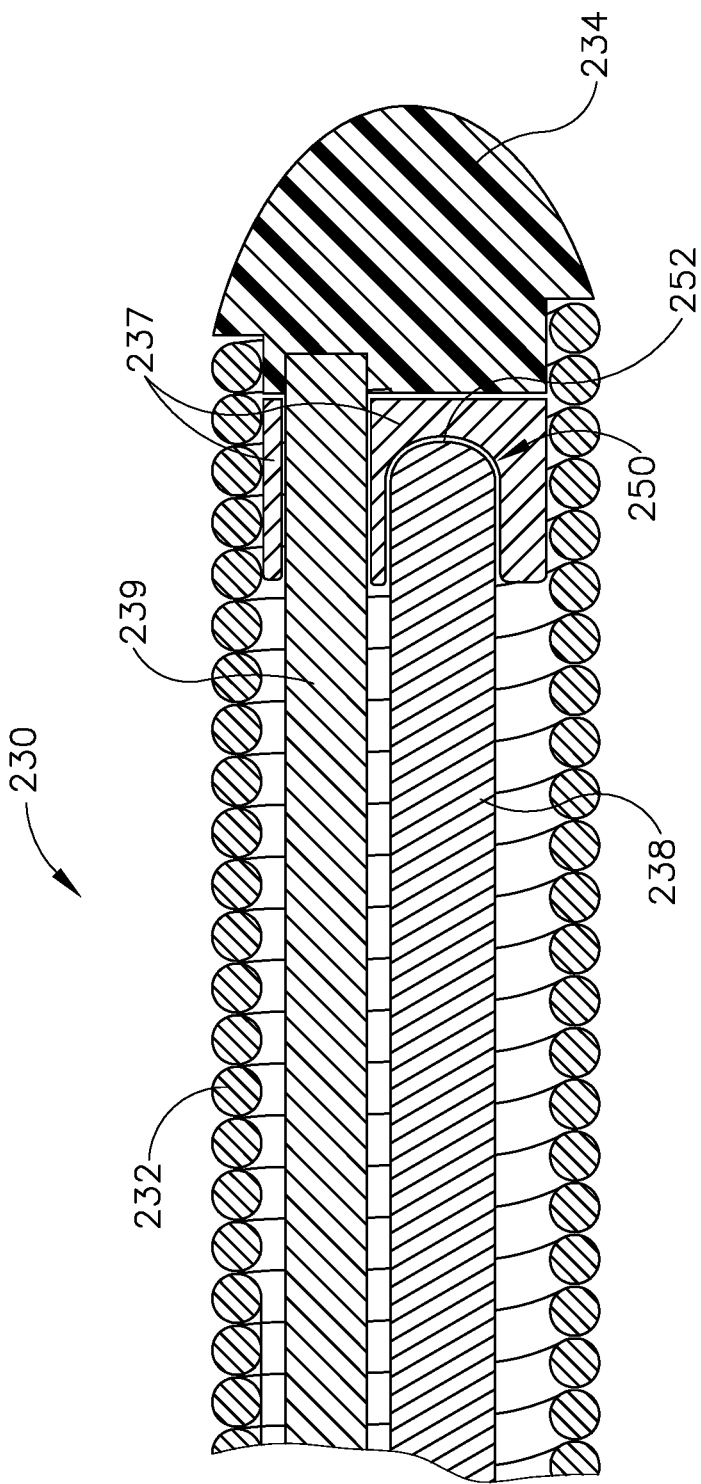
FIG. 24 depicts a side cross-sectional view of an exemplary alternative guide assembly that may be readily incorporated into the dilation catheter system of FIG. 6.
Figure 25:
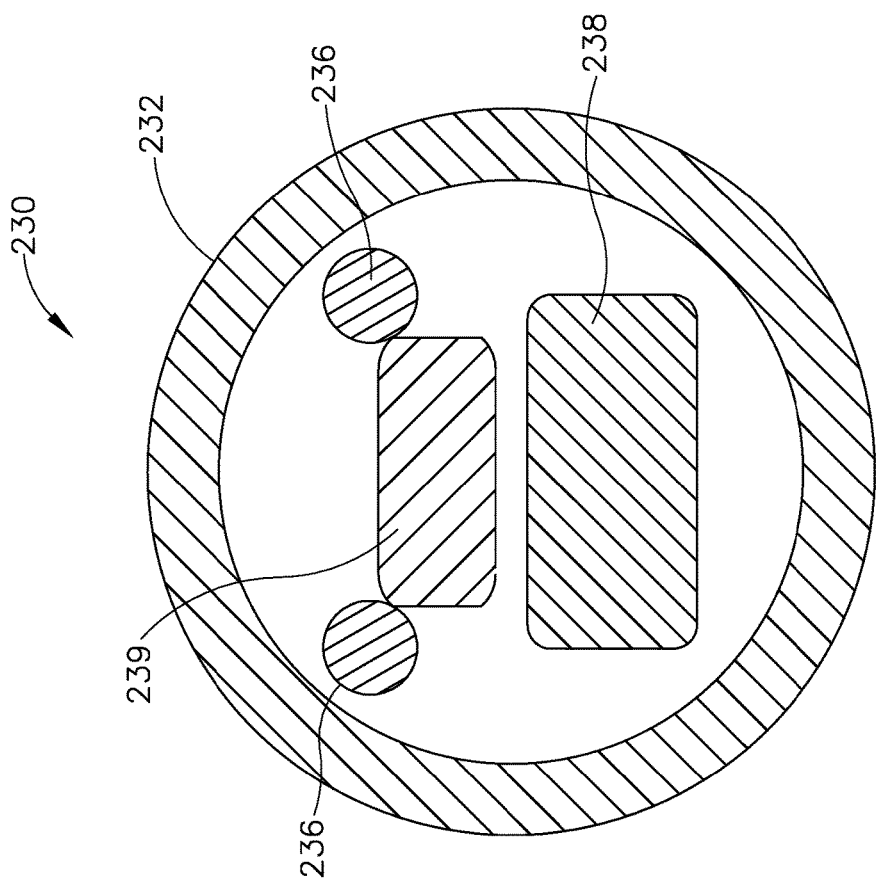
FIG. 25 depicts a front cross-sectional view of the guide assembly of FIG. 24.

FIGS. 24-25 show an exemplary alternative guide assembly (230) that may be readily incorporated into dilation instrument (100) described above. It should be understood that guide assembly (230) is substantially the same as guide assembly (130) described above unless otherwise specified herein. For instance, like guide assembly (130), guide assembly (230) of the present example comprises an external guidewire (232) and an internal guide rail (238). As in guide assembly (130) described above, guidewire (232) is slidable along guide rail (238). Guide rail (238) of this example is configured and operable substantially identical to guide rail (138) described above, such that additional details of guide rail (238) will not be discussed further. However, it should be understood that guide rail (238) may have any other suitable configuration and operability.

Guidewire (232) of the present example is substantially similar to guidewire (132) described above. For instance, like with guidewire (132) described above, guidewire (232) of the present example is generally flexible such that guidewire (232) may bendably navigate through a targeted anatomical passageway. The wire forming guidewire (232) may have any of the properties described above with respect to guidewire (132). Also like guidewire (132), guidewire (232) of the present example includes an atraumatic lens (234) affixed to the distal end of guidewire (232). Lens (234) is similar to lens (58, 134) described above. Lens (234) may be affixed to the distal end of guidewire (232) by any suitable means such as adhesive bonding, soldering, interference fitting, etc. As can best be seen in FIG. 25, two illuminating fibers (236) extend longitudinally through guidewire (232) and are in optical communication with lens (234). The proximal ends of illuminating fibers (236) may be optically coupled with a light source. Like with lens (58, 134), lens (234) is configured to project light when illumination fibers (236) are illuminated by the light source, such that illumination fibers (236) transmit light from the light source to the lens (234).

As similarly described above with respect to guidewire (132), guidewire (232) of the present example is generally configured for advancement over guide rail (238) such that guidewire (232) may be advanced while guide rail (238) remains stationary. Guidewire (232) is also configured such that dilation catheter (120) may be advanced over guidewire (232). Accordingly, it should be understood that in some examples guidewire (232) includes a coating comprising silicone or other materials to assist such advancement. Where such a coating is utilized, guidewire (232) may be coated on the both the exterior and the interior, or on either the interior or the exterior. Of course, such a coating is merely optional and in some examples guidewire (232) simply comprises bare material.

Guidewire (232) of the present example also includes a core wire (239). As with core wire (133) described above, core wire (239) of the present example provides additional structural integrity to guidewire (232). Core wire (239) comprises a solid nitinol wire having a generally ovular transverse cross-section. The particular diameter and/or thickness of core wire (239) may be selected based on the particular desired level of stiffness for guidewire (232). Core wire (239) extends longitudinally though guidewire (232) and is attached to the distal end of guidewire (232) by solder (237).

As shown in FIG. 24, solder (237) defines a pocket (250) that is configured to receive the distal end (252) of guide rail (238) when guidewire (232) is retracted to a proximal-most position. In one merely exemplary method of construction, a shaped mandrel is used during the soldering process to create pocket (250) within solder (237). Such a mandrel may comprise a material that resists adherence of solder such as polytetrafluoroethylene (PTFE), black-oxide, nitinol, etc. The distal end of the mandrel may be sized and configured just like distal end (252) of guide rail (238) such that the size and configuration of pocket (250) complements the size and configuration of distal end (252). While solder (237) is only shown at the distal end of guidewire (232), it should be understood that solder (237) may also be discretely provided at one or more other locations along at least part of the length of guidewire (232). For instance, core wire (239) may also be secured to guidewire (232) at the proximal ends of guidewire (232) and core wire (239); and/or at one or more longitudinal positions between the distal and proximal ends of guidewire (232) and core wire (239).

A modified version of instrument (100) that incorporates guide assembly (230) may be operated just like the version of instrument (100) that incorporates guide assembly (130) as described above. In particular, guide assembly (230) may be bent to a desired bend angle. Guidewire (232) may then be advanced distally along guide rail (238) along a trajectory defined by the bent guide rail (238). A dilation catheter (120) may then be advanced along guidewire (232) until dilator (122) is positioned in the targeted anatomical passageway. The dilator (122) may then be operated to dilate the anatomical passageway.

While the foregoing operations are identical to those described above with respect to the version of instrument (100) that incorporates guide assembly (130), a modified version of instrument (100) that incorporates guide assembly (230) may provide enhanced functionality when guidewire (232) is retracted to the proximal-most position. In particular, when guidewire (232) is retracted to the proximal-most position, distal end (252) of guide rail (238) is received in pocket (250) defined by solder (237). It should be understood that the positioning of distal end (252) in pocket (250) results in guide rail (238) providing enhanced rigidity to the distal end of guidewire (232). Thus, guide assembly (230) may be used like a sinus seeker device, with lens (234) and the rest of the distal end of guidewire (232) being used to probe within the nasal cavity to find sinus ostia and other anatomical passageways. When guide assembly (230) is used as a seeker device in this fashion, the positioning of distal end (252) in pocket (250) may prevent the distal end of guidewire (232) from buckling as easily as it might otherwise. This prevention of guidewire (232) buckling may result in enhanced tactile feedback to the operator when guide assembly (230) is used as a seeker device.

B. Exemplary Alternative Tubular Guide Rail and Stiffening Core Wire

Figure 26:
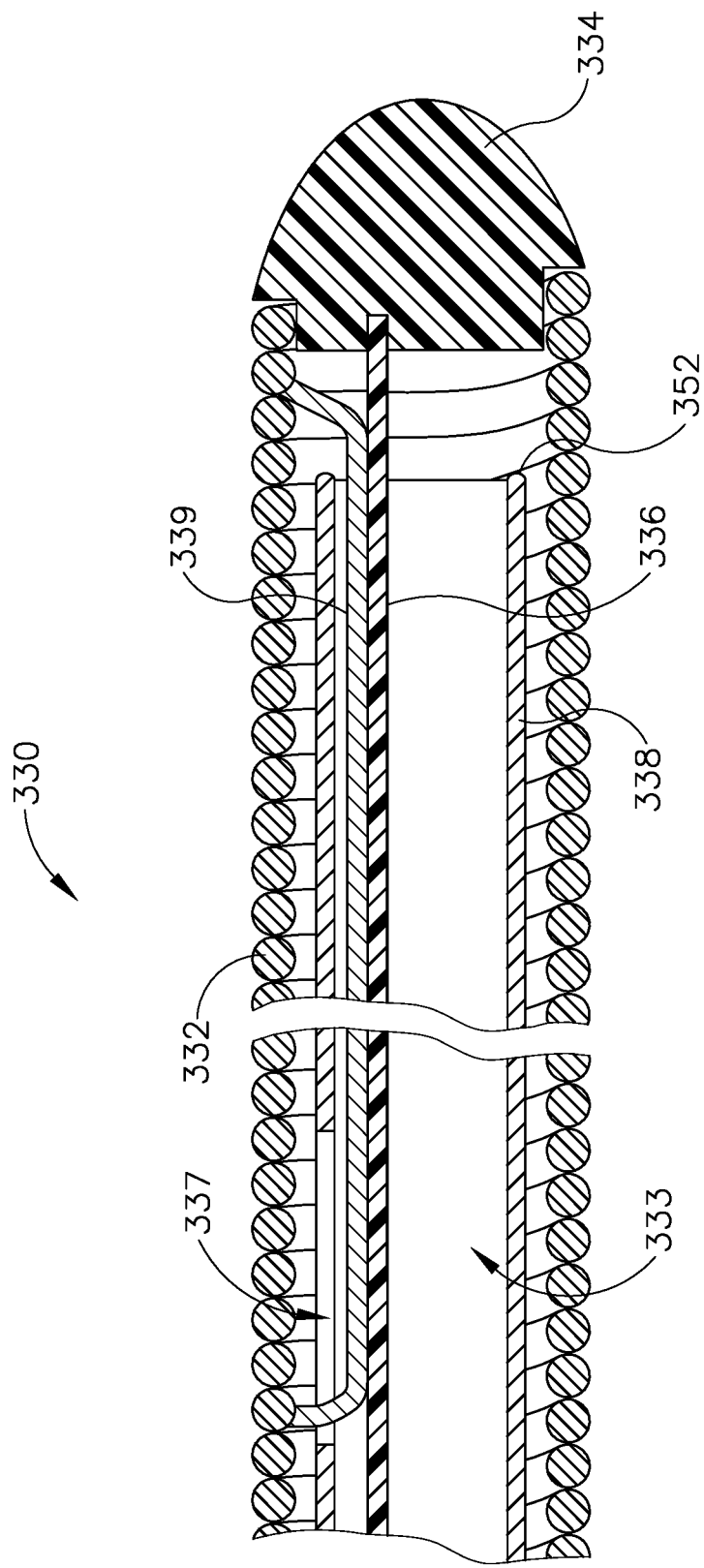
FIG. 26 depicts a side cross-sectional view of another exemplary alternative guide assembly that may be readily incorporated into the dilation catheter system of FIG. 6.
Figure 27:
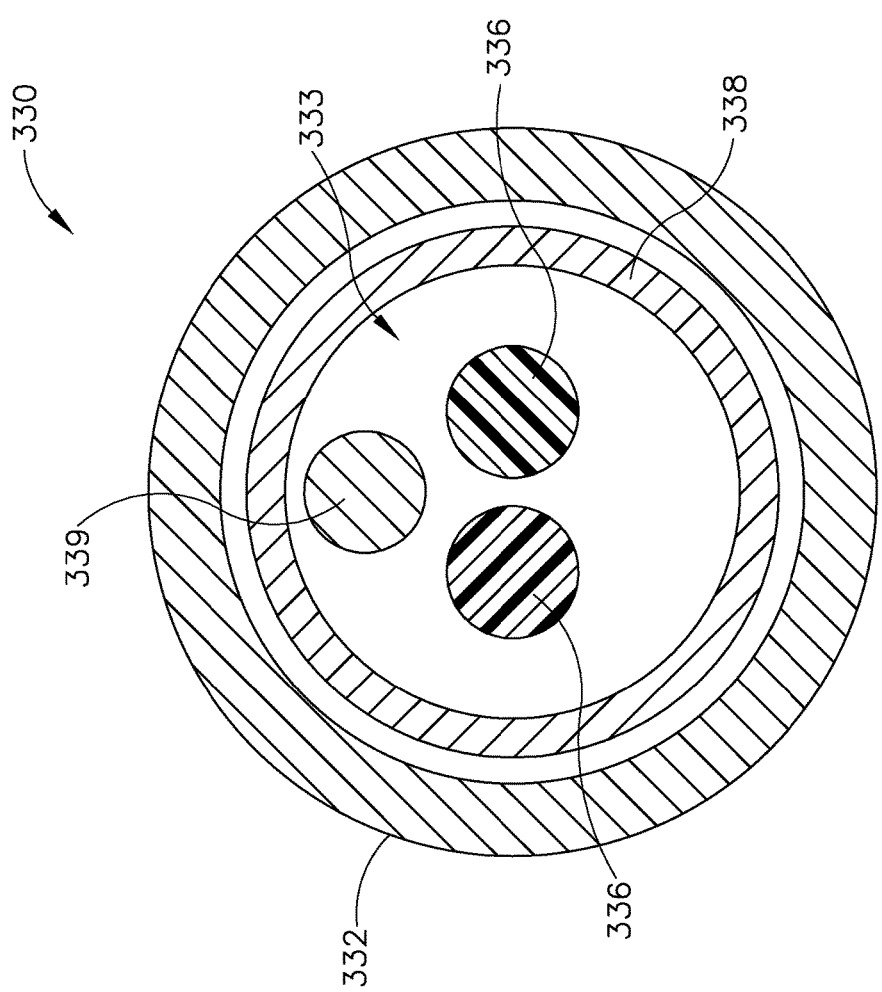
FIG. 27 depicts a front cross-sectional view of the guide assembly of FIG. 26.

FIGS. 26-27 show an exemplary alternative guide assembly (330) that may be readily incorporated into dilation instrument (100) described above. It should be understood that guide assembly (330) is substantially the same as guide assembly (130) described above unless otherwise specified herein. For instance, like guide assembly (130), guide assembly (330) of the present example comprises an external guidewire (332) and an internal guide rail (338). As in guide assembly (130) described above, guidewire (332) of the present example is generally configured for advancement over guide rail (338) such that guidewire (332) may be advanced while guide rail (338) remains stationary. Guidewire (332) is also configured such that dilation catheter (120) may be advanced over guidewire (332). Guidewire (332) of this example includes a lens (334), illuminating fibers (336), and a core wire (339). Guidewire (332) is thus configured and operable substantially identical to guidewire (132) described above, such that additional details of guidewire (332) will not be discussed further. However, it should be understood that guidewire (332) may have any other suitable configuration and operability.

Guide rail (338) of the present example is similar to guide rail (138) described above, except guide rail (338) of the present example comprises a tubular construction. In particular, guide rail (338) of the present example generally shaped as an elongate tubular rod (e.g., a hypotybe) having a generally circular transverse cross-section. The tubular shape of guide rail (338) defines a lumen (333), which receives illuminating fibers (336) and core wire (339). Guide rail (338) extends through guidewire (332) and is generally longitudinally fixed relative to handle assembly (110). By way of example only, guide rail (338) may be formed of stainless steel (e.g., SAE 304 stainless steel, SAE 316 stainless steel, etc.) that as annealed or partially annealed. Other suitable materials that may be used to form guide rail (338) will be apparent to those of ordinary skill in the art in view of the teachings herein. It should be understood that the tubular construction of guide rail (338) may provide greater stiffness than the construction of guide rail (138) described above. By way of example only, guide rail (338) may have an outer diameter of approximately 0.040 inches and an inner diameter of approximately 0.024 inches.

While guide rail (338) has a circular cross-sectional profile in this example, it should be understood that guide rail (338) may have an ovular cross-sectional profile in order to provide bendability along just one plane as described above with respect to guide rail (138). For instance, guide rail (338) may be formed of a hypotube that is laterally compressed to convert a circular cross-sectional profile into an ovular cross-sectional profile. The distal edge (352) of guide rail (338) is rounded in the present example in order to prevent guidewire (332) from snagging on distal edge (352) as guidewire is advanced and retracted longitudinally relative to guide rail (338). Like with guide rail (138) described above, guide rail (338) may also be coated to increase the slidability of guidewire (332) relative to guide rail (338). For instance, guide rail (338) may be coated with polytetrafluoroethylene (PTFE) and/or any other suitable lubricious coating.

Guide rail (338) of the present example is malleable such that guide rail (138) may be deformed to various bend angles as described above with respect to guide rail (138). As was similarly described above with respect to guide rail (138), the malleability of guide rail (338) permits an operator to manipulate guide rail (338) into a desired position to access a targeted anatomical passageway. Once guide rail (338) is bent, guidewire (332) and/or dilation catheter (120) is advanceable over guide rail (338) into position relative to the targeted anatomical passageway.

The distal end of core wire (339) is secured to the distal end of guidewire (332); while the proximal end of core wire (339) is secured to the proximal end of guidewire (332). Core wire (339) thus moves longitudinally with guidewire (332) as guidewire (332) is moved longitudinally relative to guide rail (338). The proximal end of core wire (339) extends through a slot (337) in at least a portion of the proximal end of guide rail (338). Slot (337) is configured to allow the proximal end of core wire (339) to attach to the proximal end of guidewire (332) and to allow guidewire (332) to translate relative to guide rail (338). Slot (337) is generally sized in correspondence with the travel distance of guidewire (332) relative to guide rail (338) (e.g., approximately 2 inches or 3 inches in length). Thus, the proximal attachment of core wire (339) to guidewire (332) does not inhibit movement of guidewire (332) relative to guide rail (338). In some examples, the proximal end of core wire (339) is fixedly secured to guidewire (332) by solder. Alternatively, the proximal end of core wire (339) may be secured to guidewire (332) by any other suitable means.

As another merely illustrative example, core wire (339) may be positioned outside of lumen (333), such that core wire (339) is positioned between the inner diameter of guidewire (332) and the outer diameter of guide rail (338). Slot (337) may thus be omitted in such versions. As yet another merely illustrative example, core wire (339) may simply be omitted in some versions. For instance, core wire (339) may be omitted in some versions where guidewire (332) is formed as an extrusion or cable tube, etc.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus comprising: (a) a handle assembly; (b) a guide assembly extending distally from the handle assembly, wherein the guide assembly comprises: (i) a malleable guide member having a distal end, and (ii) a flexible guide member having a distal end, wherein the distal end of the flexible guide member is distal to the distal end of the malleable guide member, wherein the flexible guide member is positioned about the malleable guide member, wherein the flexible guide member is slidable along the malleable guide member; and (c) a dilation catheter, wherein the dilation catheter is slidably disposed about the flexible guide member.

EXAMPLE 2

The apparatus of Example 1, wherein the handle assembly comprises: (i) a body, and (ii) a first actuator coupled with the flexible guide member, wherein the first actuator is movable relative to the body to selectively move the flexible guide member longitudinally relative to the malleable guide member.

EXAMPLE 3

The apparatus Example 2, wherein the handle assembly further comprises a second actuator coupled with the dilation catheter, wherein the second actuator is movable relative to the body to selectively move the dilation catheter longitudinally relative to the flexible guide member.

EXAMPLE 4

The apparatus of any one or more of Examples 1 through 3, wherein the malleable guide member is longitudinally fixed relative to the handle assembly.

EXAMPLE 5

The apparatus of any one or more of Examples 1 through 4, wherein the malleable guide member comprises a malleable wire.

EXAMPLE 6

The apparatus of Example 5, wherein the malleable wire has a non-circular cross-sectional profile.

EXAMPLE 7

The apparatus of any one or more of Examples 5 through 6, wherein the malleable wire has a rounded distal end.

EXAMPLE 8

The apparatus of any one or more of Examples 1 through 4, wherein the malleable guide member comprises a malleable tube.

EXAMPLE 9

The apparatus of Example 8, wherein the malleable tube has a circular cross-sectional profile.

EXAMPLE 10

The apparatus of Example 8, wherein the malleable tube has an ovular cross-sectional profile.

EXAMPLE 11

The apparatus of any one or more of Examples 8 through 10, wherein the guide assembly further comprises one or more optical fibers.

EXAMPLE 12

The apparatus of Example 11, wherein the one or more optical fibers extend through a lumen defined by the malleable tube.

EXAMPLE 13

The apparatus of any one or more of Examples 8 through 12, wherein the guide assembly further comprises a core wire, wherein the core wire is secured to the flexible guide member.

EXAMPLE 14

The apparatus of Example 13, wherein the core wire extends through a lumen defined by the malleable tube.

EXAMPLE 15

The apparatus of Example 14, wherein the malleable tube defines a transverse slot, wherein a proximal portion of the core wire extends through the transverse slot.

EXAMPLE 16

The apparatus of any one or more of Examples 1 through 15, wherein the malleable guide member is rotatable relative to the handle assembly about a longitudinal axis defined by the malleable guide member.

EXAMPLE 17

The apparatus of any one or more of Examples 1 through 16, wherein the flexible guide member comprises a guidewire.

EXAMPLE 18

The apparatus of Example 17, wherein the guidewire comprises a wire wound to form a coil.

EXAMPLE 19

The apparatus of any one or more of Examples 1 through 18, wherein the flexible guide member comprises an optically transmissive polymeric material.

EXAMPLE 20

The apparatus of any one or more of Examples 1 through 19, wherein the flexible guide member has a distal tip configured to transmit light.

EXAMPLE 21

The apparatus of any one or more of Examples 1 through 20, wherein the distal end of the flexible guide member has a rigid tip receiving member defining a proximally presented pocket, wherein the proximally presented pocket is configured to receive the distal end of the malleable guide member.

EXAMPLE 22

The apparatus of Example 21, wherein the tip receiving member comprises a solder material.

EXAMPLE 23

The apparatus of any one or more of Examples 1 through 22, wherein the guide assembly is configured to provide tactile feedback indicative of a bend angle formed in the guide assembly.

EXAMPLE 24

The apparatus of Example 23, wherein the guide assembly further comprises two or more angle stops configured to provide tactile feedback associated with two or more predetermined bend angles.

EXAMPLE 25

The apparatus of any one or more of Examples 1 through 24, wherein the guide assembly further comprises a visual indicator configured to provide visual indication of an inside of a bend formed in guide assembly.

EXAMPLE 26

The apparatus of any one or more of Examples 1 through 25, wherein the handle assembly comprises a steering member operable to selectively deform the malleable guide member to thereby selectively define a bend angle in the guide assembly.

EXAMPLE 27

The apparatus of any one or more of Examples 1 through 26, wherein the malleable guide member is configured to bend along only one orthogonal plane.

EXAMPLE 28

A method of operating an instrument to dilate a targeted anatomical passageway in a patient, the method comprising: (a) bending a guide assembly to achieve a bend angle, wherein the bend angle is selected to orient a distal end of the guide assembly toward the targeted anatomical passageway, wherein the guide assembly comprises: (i) a malleable guide member having a distal end, and (ii) a flexible guide member having a distal end; (b) inserting the distal end of the guide assembly through a nostril of a patient while the guide assembly is bent at the selected bend angle; (c) orienting the distal end the guide assembly toward the targeted anatomical passageway while the distal end of the guide assembly is positioned in the patient; (d) advancing the flexible guide member along the malleable guide member to position a portion of the flexible guide member in the targeted anatomical passageway; (e) advancing a dilation catheter along the advanced flexible guide member to thereby position an expandable element of the dilation catheter in the targeted anatomical passageway; and (f) expanding the expandable element in the targeted anatomical passageway.

EXAMPLE 29

The method of Example 28, wherein the selected bend angle is approximately 30°.

EXAMPLE 30

The method of Example 29, wherein the targeted anatomical passageway comprises a sphenoid sinus ostium.

EXAMPLE 31

The method of Example 28, wherein the selected bend angle is approximately 70°.

EXAMPLE 32

The method of Example 31, wherein the targeted anatomical passageway comprises a frontal recess associated with a frontal sinus.

EXAMPLE 33

The method of Example 28, wherein the selected bend angle is between approximately 110° and approximately 130°.

EXAMPLE 34

The method of Example 33, wherein the targeted anatomical passageway comprises a maxillary sinus ostium.

EXAMPLE 35

The method of Example 28, wherein the selected bend angle is approximately 55°.

EXAMPLE 36

The method of Example 35, wherein the targeted anatomical passageway comprises a Eustachian tube.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a handle assembly;
   (b) a guide assembly extending distally from the handle assembly, wherein the guide assembly comprises:
      (i) a malleable guide member having a distal end, wherein the malleable guide member is configured to assume and maintain a bent shape relative to a longitudinal axis of the guide assembly, and
      (ii) a flexible guide member having a distal end, wherein the distal end of the flexible guide member is distal to the distal end of the malleable guide member, wherein the flexible guide member is slidably disposed positioned about the malleable guide member, wherein an entirety of the flexible guide member is translatable relative to the malleable guide member to advance the distal end of the flexible guide member relative to the distal end of the malleable guide member, wherein a portion of the flexible guide member is slidable along the malleable guide member; and
   (c) a dilation catheter, wherein the dilation catheter is slidably disposed about the flexible guide member, wherein the flexible guide member and the dilation catheter are slidable independently of one another relative to the malleable guide member via the handle assembly.

2. The apparatus of claim 1, wherein the handle assembly comprises:
   (i) a body,
   (ii) a first actuator coupled with the flexible guide member, wherein the first actuator is movable relative to the body to selectively move the flexible guide member longitudinally relative to the malleable guide member, and
   (iii) a second actuator coupled with the dilation catheter, wherein the second actuator is movable relative to the body to selectively move the dilation catheter longitudinally relative to the flexible guide member.

3. The apparatus of claim 1, wherein the malleable guide member is longitudinally fixed relative to the handle assembly.

4. The apparatus of claim 1, wherein the malleable guide member comprises a malleable wire.

5. The apparatus of claim 4, wherein the malleable wire has a non-circular cross-sectional profile.

6. The apparatus of claim 4, wherein the malleable wire has a rounded distal end.

7. The apparatus of claim 1, wherein the malleable guide member comprises a malleable tube.

8. The apparatus of claim 7, wherein the guide assembly further comprises one or more optical fibers.

9. The apparatus of claim 8, wherein the one or more optical fibers extend through a lumen defined by the malleable tube.

10. The apparatus of claim 1, wherein the guide assembly further comprises a core wire, wherein the core wire is secured to the flexible guide member.

11. The apparatus of claim 1, wherein the malleable guide member is rotatable relative to the handle assembly about a longitudinal axis defined by the malleable guide member.

12. The apparatus of claim 1, wherein the flexible guide member comprises a guidewire.

13. The apparatus of claim 12, wherein the guidewire comprises a wire wound to form a coil.

14. The apparatus of claim 1, wherein the flexible guide member comprises an optically transmissive polymeric material.

15. The apparatus of claim 1, wherein the flexible guide member has a distal tip configured to transmit light.

16. The apparatus of claim 1, wherein the guide assembly further comprises two or more angle stops configured to provide tactile feedback associated with two or more predetermined bend angles.

17. An apparatus comprising:
   (a) a guide assembly comprising:
      (i) a malleable guide member having a distal end, wherein a bending portion of the malleable guide member is configured to assume and maintain a bend angle relative to a longitudinal axis of the guide assembly, and (ii) a flexible guide member having a distal end, wherein the distal end of the flexible guide member is distal to the distal end of the malleable guide member, wherein the flexible guide member is positioned about the malleable guide member such that the malleable guide member is positioned within the flexible guide member, wherein an entirety of the flexible guide member is translatable relative to the malleable guide member, wherein a portion of the flexible guide member is slidable along the malleable guide member and over the bending portion thereof while the malleable guide member maintains the bend angle; and (c) a dilation catheter, wherein the dilation catheter is slidably disposed about the flexible guide member such that the flexible guide member is positioned within the dilation catheter, wherein the dilation catheter is dimensioned to fit within a passageway associated with a paranasal sinus, (d) a handle assembly; wherein the flexible guide member and the dilation catheter are slidable independently of one another relative to the malleable guide member via the handle assembly.

18. The apparatus of claim 17, wherein the malleable guide member is configured to bend along only one orthogonal plane.

19. A method of operating an instrument to dilate a targeted anatomical passageway in a patient, the method comprising:

(a) before inserting the instrument into a patient, bending a guide assembly to achieve and maintain a bend angle, wherein the bend angle is selected to orient a distal end of the guide assembly toward the targeted anatomical passageway, wherein the guide assembly comprises:
  (i) an inner malleable guide member having a bending portion and a distal end, wherein bending the guide assembly includes bending the bending portion, and
  (ii) an outer flexible guide member slidably disposed over the malleable guide member and having a distal end;

(b) inserting the distal end of the guide assembly through a nostril of the patient while the guide assembly remains bent at the selected bend angle;

(c) orienting the distal end of the guide assembly toward the targeted anatomical passageway while the distal end of the guide assembly is positioned in the patient;

(d) translating an entirety of the flexible guide member distally relative to the malleable guide member such that a portion of the flexible guide member slides along the bent bending portion of the malleable guide member to position a portion of the flexible guide member in the targeted anatomical passageway;

(e) advancing a dilation catheter along the advanced flexible guide member to thereby position an expandable element of the dilation catheter in the targeted anatomical passageway; and (f) expanding the expandable element in the targeted anatomical passageway.

20. The apparatus of claim 17, further comprising a bend angle feature configured to provide tactile feedback when the malleable guide member first assumes the bend angle.

\* \* \* \* \*